(12) United States Patent
Bessette et al.

(10) Patent No.: US 7,109,240 B2
(45) Date of Patent: Sep. 19, 2006

(54) NON-HAZARDOUS PEST CONTROL

(75) Inventors: Steven M. Bessette, Brentwood, TN (US); Arthur M. Knight, Alpharetta, GA (US)

(73) Assignee: Ecosmart Technologies, Inc., Franklin, TN (US)

( * ) Notice: Subject to any disclaimer, the term of this patent is extended or adjusted under 35 U.S.C. 154(b) by 311 days.

(21) Appl. No.: 10/810,859

(22) Filed: Mar. 29, 2004

(65) Prior Publication Data

US 2005/0004233 A1    Jan. 6, 2005

Related U.S. Application Data

(60) Division of application No. 09/578,724, filed on May 26, 2000, now Pat. No. 6,713,518, which is a continuation-in-part of application No. 08/657,585, filed on Jun. 7, 1996, now Pat. No. 6,114,384, which is a continuation-in-part of application No. PCT/US94/05823, filed on May 20, 1994, which is a continuation-in-part of application No. 08/065,594, filed on May 21, 1993, now Pat. No. 5,439,690.

(51) Int. Cl.
*A01N 37/02* (2006.01)
*A01N 31/04* (2006.01)
*A61P 33/00* (2006.01)
*A61P 33/14* (2006.01)

(52) U.S. Cl. .................... 514/546; 514/730; 514/875; 514/919; 424/DIG. 10; 424/DIG. 11; 424/84

(58) Field of Classification Search ............... 514/546, 514/730, 875, 919; 424/84, DIG. 10, DIG. 11
See application file for complete search history.

(56) References Cited

U.S. PATENT DOCUMENTS 3,931,341 A    1/1976    Brady et al.
6,531,163 B1 *   3/2003   Bessette et al. ............. 424/747
6,713,518 B1 *   3/2004   Bessette et al. ............. 514/730
6,849,614 B1 *   2/2005   Bessette et al. ............... 514/72

OTHER PUBLICATIONS

Webster's Third New International Dictionary of the English Language Unabridged, Merriam-Webster Inc., Springfield, Massachusetts, 1986, p. 2509, definition of "unscented."*

'Tetrahydrofurfuryl alcohol (THFA) for use in crop production.' National Organic Standards Board Technical Advisory Panel Review. May 5, 2003 [Retrieved on Mar. 31, 2006]. Retrieved from the internet:, URL: www.arms.usda.gov/nop/NationalList/THFATAP.pdf.*

HCAPLUS Abstract 1983:174818 (1983).*
CABA Abstract 82:24729 (1982).*
CABA Abstract 2002:16356 (2002).*
HCAPLUS Abstract 1992:464791 (1992).*
HCAPLUS Abstract 2000:777822 (2000).*
King, W. V. et al., "Chemicals evaluated as insecticides and repellants at Orlando, FL", Agriculture Handbook, No. 69, U.S. Department of Agriculture, p. 1-17 and 82 (May 1954).

* cited by examiner

*Primary Examiner*—John Pak
(74) *Attorney, Agent, or Firm*—Nixon & Vanderhye P.C.

(57) ABSTRACT

Disclosed is a method for killing or controlling invertebrates comprising applying a pesticidally-effective amount of a pesticidal composition to invertebrates or to a locus where killing or control of invertebrates is desired, wherein (i) the invertebrates are selected from the group consisting of ants, cockroaches, spiders, fleas, ticks, earwigs, pillbugs, beetles, flies, crickets, mosquitoes, and wasps, and (ii) the pesticidal composition is unscented and comprises an inert carrier and a pesticidally active ingredient consisting of benzyl alcohol and phenethyl propionate.

16 Claims, No Drawings

NON-HAZARDOUS PEST CONTROL

CROSS REFERENCE TO RELATED APPLICATIONS

This application is a divisional of U.S. patent application Ser. No. 09/578,724, filed May 26, 2000, now U.S. Pat. No. 6,713,518, which is a continuation-in-part of U.S. patent application Ser. No. 08/657,585, filed Jun. 7, 1996, now U.S. Pat. No. 6,114,384, which is, in turn, a continuation-in-part of International Application No. PCT/US94/05823, filed May 20, 1994, and the corresponding U.S. National Phase Ser. No. 08/553,475, filed Nov. 9, 1995, now U.S. Pat. No. 5,693,344, which is, in turn, a continuation-in-part of U.S. patent application Ser. No. 08/065,594, filed May 21, 1993, now U.S. Pat. No. 5,439,690.

FIELD OF THE INVENTION

The present invention relates, in general, to pesticidal compositions containing plant essential oils. In one aspect, the present invention relates to pesticidal compositions containing one or more plant essential oils and/or derivatives thereof to be used as a contact pesticide and/or repellent. In a further aspect, the present invention relates to a method for controlling pests by the application of pesticidally effective amounts of the pesticidal compositions to a locus where pest control is desired.

BACKGROUND OF THE INVENTION

The present invention relates to the control of pests and, more particularly, to a non-hazardous pest control agent (a.k.a. pesticide) that eliminates pests through either neural effects of a component or mechanical puncture of the exoskeleton and also, through the neurally effective component entering the puncture. Throughout this description, the term "pest" shall include, without limitation, insects and arachnids.

Insects and other pests have long plagued humankind. Over the years, various approaches have been taken to control pests and especially insects, and none have been completely satisfactory.

For example, the use of complex, organic insecticides, such as disclosed in U.S. Pat. Nos. 4,376,784 and 4,308,279, are expensive to produce, can be hazardous to man, domestic animals, and the environment, and frequently are effective only on certain groups of insects. Moreover, the target insects often build an immunity to the insecticide.

Another approach employs absorbent organic polymers for widespread dehydration of the insects. See, U.S. Pat. Nos. 4,985,251; 4,983,390; 4,818,534; and 4,983,389. However, this approach is limited predominantly to aquatic environments, and it likewise relies on hazardous chemical insecticidal agents. Further, the addition of essential oils is primarily as an insect attractant.

In addition, this approach is based on the selective absorption of a thin layer of insect wax from the exoskeleton and not to a puncture of the exoskeleton. [Sci. Pharm. Proc. 25th, Melchor et al, pp. 589–597 (1966)].

The use of inorganic salts as components of pesticides is reported by U.S. Pat. Nos. 2,423,284 and 4,948,013, European Patent Application No. 462 347, Chemical Abstracts 119(5):43357q (1993) and Farm Chemicals Handbook, page c102 (1987). These references disclose the inclusion of these components but not the puncturing of the exoskeleton of the insect by the salts.

The applicants are also aware of the following which disclose pesticides and insecticides: U.S. Pat. Nos. 4,806,526, 4,834,977, 5,110,594, 5,271,947 and 5,342,630.

The marketplace is replete with toxic chemical insecticidal agents that are offensive to apply and, more importantly, pose a danger to humans and the environment.

It would be greatly advantageous to solve these problems with a pesticidal agent/composition that works neurally and with a penetrating substance to kill pests, thereby eliminating the need for any chemicals which are toxic to humans and domestic animals.

SUMMARY OF THE INVENTION

Accordingly, it is an object of the invention to provide a method for non-hazardous pest control and a composition for the same which kills pests neurally and both mechanically and neurally.

It is another object to provide a safe, non-toxic pest control agent that will not harm the environment.

It is another object to provide a pest control agent that is highly effective in combating a wide variety of pests, including all insects and arachnids having an exoskeleton.

It is another object to provide a pest control agent which has either no scent or a pleasant scent, and which can be applied without burdensome safety precautions for humans and domestic animals.

It is still another object to provide a pest control agent as described above which can be inexpensively produced.

It is yet another object of the invention to provide a pest control agent to which pests cannot build an immunity.

In accordance with the above-described and other objects, the present invention provides a pesticide for insects and arachnids comprising a carrier and at least a neurally effective substance. The neurally effective substance has the following Formula

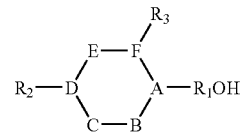

wherein $R_1$ is any of the following: $CH_2$, $C_2H_4$, $C_3H_6$, $C_3H_4$, $C_4H_8$ or $C_4H_4$, $R_2$ is any of the following: H, $H_2$, $CH_3$, $C_2H_5$, $C_3H_7$, $C_3H_5$, $C_4H_9$ or $C_4H_5$, $R_3$ is any of the following: H, $H_2$ or $OCH_3$, and wherein the six member ring ABCDEF has at least one unsaturated bond therein.

During the course of developing improved insecticidal compositions the inventors have found that various organic compounds when applied in a novel manner will unexpectedly act as a pesticide to kill insects and arachnids. Among the preferred compounds that applicants have found to be insecticidal are terpeniol, phenylethyl alcohol, benzyl acetate, benzyl alcohol, eugenol and cinnamic alcohol. To be affective these compounds should be incorporated into carriers preferably in the form of aerosols, dusts, solutions, liquid emulsions and the like.

The herein disclosed invention envisions a pesticide for insects and arachnids comprising a carrier and an effective amount of at least one neurally effective substance. In a specific embodiment the carrier is crystalline dust having a size effective to puncture the exoskeleton and to permit the neurally effective substance to enter the punctured exoskeleton and interfere with the bodily function of the insects and arachnids. Specifically the carrier can be a crystalline powder of a mixture of alkali metal bicarbonate, calcium carbonate, diatomaceous earth and amorphous silica. The crystalline powder has a particle size of 0.1 to 200 microns, and preferably under 100 microns, and the calcium carbonate can be in the form of ground pottery glaze. In an alternative embodiment the carrier is an aerosol spray having a solvent and a propellant, and is compatible and non-reactive with the neurally effective substance. Specifically the solvent can be an organic solvent, either aromatic or aliphatic, and wherein the propellant is carbon dioxide or dimethyl ether. It is to be understood that the solvent is compatible and nonreactive with the neurally effective substances. The neurally effective substances in the composition can be in the range of approximately 0.01% to 10% by weight of the pesticide composition. In some embodiments of the pesticidal composition the neurally effective substance is a mixture of two or more neurally effective substances and/or other diluents included for aesthetic purposes.

In an alternative embodiment of the pesticide for controlling insects and arachnids the composition comprises an effective amount of crystalline powder including calcium carbonate, alkali metal bicarbonate, absorbent material and at least one neurally effective substance having a chemical structure represented by the formula 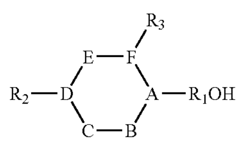 wherein $R_1$ is any of the following: $CH_2$, $C_2H_4$, $C_3H_6$, $C_3H_4$, $C_4H_8$ or $C_4H_4$, $R_2$is any of the following: H, $H_2$, $CH_3$, $C_2H_5$, $C_3H_7$, $C_3H_5$, $C_4H_9$ or $C_4H_5$, $R_3$ is any of the following: H, $H_2$ or $OCH_3$, and wherein the six member ring ABCDEF has at least one unsaturated bond therein and also an ester of the hydroxyl group on $R_1$ when $R_1$ is $CH_2$, $R_2$is H and $R_3$is H, and specifically an acetate ester. The pesticide formulation contains the neurally effective substance in 0.1% to 10% or more by weight of the pesticide. The crystalline powder of this composition comprises calcium carbonate 27%–35%, sodium bicarbonate 54%–65% and absorbent material 4%–5% by weight.

In a particularly elegant embodiment of this invention the pesticide for controlling insects and arachnids comprises an aerosol spray including a solvent, a propellant and an effective amount of at least one neurally effective substance having a chemical structure of 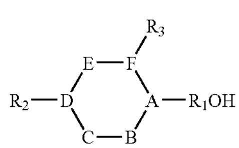 wherein $R_1$ is any of the following: $CH_2$, $C_2H_4$, $C_3H_6$, $C_3H_4$, $C_4H_8$ or $C_4H_4$, $R_2$ is any of the following: H, $H_2$, $CH_3$, $C_2H_5$, $C_3H_7$, $C_3H_5$, $C_4H_9$ or $C_4H_5$, $R_3$ is any of the following: H, $H_2$ or $OCH_3$, and wherein the six member ring ABCDEF has at least one unsaturated bond therein and wherein the neurally effective substance can be an ester of the hydroxyl group on $R_1$ when $R_1$ is $CH_2$, $R_2$ is H and $R_3$ is H. Specifically the ester is an acetate ester. The neurally effective substance is present in 0.1% to 10% or more by weight of the pesticide. The propellant can be carbon dioxide. The solvent can be an organic solvent. The pesticide for insects and arachnids can contain a solvent and at least one neurally effective substance. In preferred embodiments the compositions are an insecticidal aerosol formulation comprising as the active ingredient a member of the group consisting of terpineol, phenyl ethyl alcohol, benzyl acetate, benzyl alcohol, eugenol, cinnamic alcohol and mixtures thereof contained in an aerosol container including a propellant and a solvent.

The above and other objects are accomplished by the present invention, which is directed to pesticidal compositions comprising plant essential oils and/or derivatives thereof, natural or synthetic, in admixture with suitable carriers. In addition, the present invention is directed to a method for controlling pests by applying a pesticidally-effective amount of the above pesticidal compositions to a locus where pest control is desired.

Additional objects and attendant advantages of the present invention will be set forth, in part, in the description that follows, or may be learned from practicing or using the present invention. The objects and advantages may be realized and attained by means of the instrumentalities and combinations particularly recited in the appended claims. It is to be understood that the foregoing general description and the following detailed description are exemplary and explanatory only and are not to be viewed as being restrictive of the invention, as claimed.

DETAILED DESCRIPTION OF PREFERRED EMBODIMENTS

All patents, patent applications and literatures cited in this description are incorporated herein by reference in their entirety.

Neurally effective/active substances/compounds encompassed within the present invention may comprise the general structural Formula 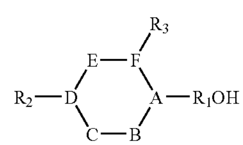 wherein $R_1$ is $CH_2$, $C_2H_4$, $C_3H_6$, $C_3H_4$, $C_4H_8$ or $C_4H_4$ $R_2$ is H, $H_2$, $CH_3$, $C_2H_5$, $C_3H_7$, $C_3H_5$, $C_4H_9$ or $C_4H_5$ $R_3$ is H, $H_2$ or $OCH_3$, and The six member ring ABCDEF has at least one unsaturated bond therein. The neurally active substances may also be an ester of the hydroxyl group on $R_1$. Mixtures of several neurally effective substances have been found to be effective.

In one embodiment, the present invention provides a pesticidal composition in admixture with a suitable carrier and optionally with a suitable surface active agent, comprising one or more neurally effective substance/compound of the above-described Formula and derivatives thereof, natural or synthetic, including racemic mixtures, enantiomers, diastereomers, hydrates, salts, solvates and metabolites, etc. The neurally effective substance or derivative thereof, may be comprised of a monocyclic, carbocyclic ring structure having six-members and is substituted by at least one oxygenated or hydroxyl functional moiety. Non-limiting examples of neurally effective substances encompassed within the present invention, include members selected from the group consisting of aldehyde C16 (pure), α-terpineol, amyl cinnamic aldehyde, amyl salicylate, anisic aldehyde, benzyl alcohol, benzyl acetate, cinnamaldehyde, cinnamic alcohol, carvacrol, carveol, citral, citronellal, citronellol, p-cymene, diethyl phthalate, dimethyl salicylate, dipropylene glycol, eucalyptol (cineole), eugenol, iso-eugenol, galaxolide, geraniol, guaiacol, ionone, menthol, methyl anthranilate, methyl ionone, methyl salicylate, α-phellandrene, pennyroyal oil, perillaldehyde, 1- or 2-phenyl ethyl alcohol, 1- or 2-phenyl ethyl propionate, piperonal, piperonyl acetate, piperonyl alcohol, D-pulegone, terpinen-4-ol, terpinyl acetate, 4-tert butylcyclohexyl acetate, thyme oil, thymol, metabolites of trans-anethole, vanillin, ethyl vanillin, and the like. The plant essential oils may also include known compounds such as pyrethrins, neem oil, d-limonene, and citronella oil. Particularly preferred examples of neurally effective substances include members selected from the group consisting of: benzyl alcohol, benzyl acetate, phenyl ethyl alcohol, terpineol, cinnamic alcohol, phenol and eugenol. As these compounds are known and used for other purposes, they may be prepared or obtained by a skilled artisan by employing known methods or sources.

The effective concentration of the active ingredient will generally be in the range of 0.01% to 10% and will be the primary active ingredient or function as a synergist. It is to be understood that various known active synergists can be added to the disclosed compositions of this invention to enhance the insecticidal activity of the composition.

The compositions encompassed by this invention will find application for indoor application as well as outdoor application. The composition can be formulated as a "pet cologne" for application to pets. An odorless composition is contemplated; as well as compositions formulated to avoid allergic reactions. The floral fragrances contemplated by this invention are limitless.

None of the individual components are identified by the United States Environmental Protection Agency as having active insecticidal properties. All are considered to be inert in and of themselves at the concentration disclosed herein. Thus, the demonstration of toxic effects on pests is considered to be unexpected.

Applicants do not wish to be bound to the theory of neural activity.

If the pesticide of the present invention is liberally administered in the vicinity of the insects, it cannot be avoided by the insects and death is imminent. Moreover, it is impossible for the insects to build an immunity to the composition.

Most insects have an exoskeleton, cuticle or outer shell which has an outer waxy coating. There are microscopic wax canals in the cuticle. The exoskeleton typically comprises multiple body plates joined together by cartilaginous membrane. This thin shell and the waxy coating is the primary protection the insect has to insure the maintenance of its vital body fluids. If an insect loses as little as 10% of these fluids, it will die.

The exoskeleton provides protection against most foreign agents such as pesticidal liquids and powders. For this reason, ingestion is the primary method of delivery for conventional pesticides and may also be a method of delivery of the pesticide of the present invention. However, pests will only ingest certain substances and in small amounts. This imposes limits on the types of usable pesticides and their effectiveness. For instance, insects generally will not ingest fatal amounts of dehydrating pesticide.

The present invention proposes new methods of delivery of a pesticide for insects and arachnids. The pesticide is at least one neurally effective chemical having a functional hydroxyl group in the proximity of a six member carbon ring. The neurally effective chemical, it is believed, is capable of dissolving or in some manner, penetrating the cuticle or waxy coated exoskeleton such that the hydroxyl group of the chemical interacts or binds with a vital substance within the insect or arachnid. This binding is fatal to the insect or arachnid. The neurally effective chemical is dispersed in a carrier which may be a dust, aerosol, emulsion or solvent carrier. The aerosol carrier and the liquid carrier provide an effective media to expose the insect or arachnid to the neurally effective chemical. The dust media provides a carrier to mechanically puncture the exoskeleton and accelerate the interaction between the neurally active chemical and the vital substance within the insect or arachnid. The dust media also is a dehydrating agent which provides another mode for killing the insect or arachnid.

A dust media containing diatomaceous earth, sodium bicarbonate, calcium carbonate and amorphous silica affect most insects very slowly, usually over several hours. Symptomology of exposure to these dusts is a gradual reduction in activity, slow loss of weight, and eventual death. These dusts do not provide rapid or sudden "knockdown".

Diatomaceous earth is a mild abrasive and desiccant. It abraids the cuticle and adsorbs the outer epicuticlar wax layer of several kinds of insects. Some, but not all, insects that lose the protective wax layer under dry conditions succumb within hours from evaporative loss of body water through the remaining integument. Unaffected insects may have a protective basal cement layer in the cuticle that affords additional protection from desiccation. Because some insects may replace surface wax quickly, a mild desiccant such as diatomaceous earth is not effective when the air is moist and has little evaporative power. Even when effective against insects, diatomaceous earth works fairly slowly.

A synergistic effect of calcium carbonate and calcium carbonate with other ingredients is possible, but unlikely. Rapid knockdown or paralysis of insects exposed to heavy deposits of either of these dusts has not been observed.

By their physical nature, several kinds of lightweight dusts with small pore size (i.e. very small particle size) that are not ordinarily considered desiccants may adsorb insect wax, in a similar fashion to diatomaceous earth. Adsorption eventually leads to lethal desiccation if the insect cannot replace the lost cuticular wax.

The rapid knockdown observed with the dust embodiment of the present pesticide is probably the result of an interaction between one or more of the dusts and a nerve-active substance, rather than from desiccation per se. The neurally effective substance may be the nerve-active substance. Once deposited on an insect, some dusts create a "water continuum" between the inside and outside of the insect.

Hemolymph, in the form of lipid-water liquid crystals, is drawn by the dust to the surface from the interior of the insect through microscopic wax canals in the cuticle. Substances carried in the dust may then pass through the continuum into the insect where they come in contact with nerves bathed by the hemolymph. This process may occur very rapidly.

Another possibility of action is that the dust components facilitate rapid penetration of an active substance through the cuticle. Oily and alcoholic substances such as the neurally effective substance reported herein may readily penetrate thin or untanned portions of cuticle. The dusts may act as a dust diluent for a more "active" compound. Nonsorptive dusts such as diatomaceous earth tend to be effective diluents because they do not bind substances too tightly, thereby making the substance they carry available to the insect surface. Nerves near spiracles or other sensitive sites may be quickly affected, and may result in rapid knockdown, paralysis or death.

Bear in mind that the dust composition of this application, unlike previous dust compositions do not have to be boiled or cooked.

The powder (or dust) embodiment is preferably prepared by processing and/or mixing the crystalline solids [alkali metal bicarbonate (54%–65%), calcium carbonate (27%–35%), amorphous silica (1%–3%) and diatomaceous earth (4%–5%)] in a ribbon blender for approximately five to fifteen minutes to obtain a particle size of approximately 1–100 microns and the neurally effective substance (or substances) is then intimately mixed with the blend of crystalline solids. The amorphous silica known as HiSil(R) 233 marketed by Harwick, Akron, Ohio has been used satisfactorily.

The aerosol embodiment is preferably prepared by mixing the active neurally effective substance or substances (1%–7%) with a solvent such as a mixture of paraffin hydrocarbons (50%–95%). Isoparaffinic hydrocarbons sold by Exxon Corporation known as Isopar H, Isopar L and Isopar M have been used satisfactorily but the solvent is not limited to these products. The mix is introduced into an aerosol container together with a propellant such as carbon dioxide, dimethyl ether, propane or a propane-butane mixture (5%–18%). All proportions are by weight.

The liquid formulation or solvent embodiment is preferably prepared by mixing the active neurally effective substance or substances (1%–5%) with the isoparaffin hydrocarbon solvent (75%–99%) and placing the mix into a container which can be used for dispensing the liquid.

Use of pesticidal compositions of the present invention generally results in 100% mortality on contact, along with good repellency and residual control. As such, they are advantageously employed as pesticidal agents in uses such as, without limitation, shampoos, hair gels, body cremes, lotions, and other on-skin applications for the treatment of head lice, body lice, and pubic lice. They may also be used in combination with other pesticidally active compounds, to increase efficacy and/or reduce toxicity, generally making conventional pesticides more acceptable.

The term "carrier" as used herein means an inert or fluid material, which may be inorganic or organic and of synthetic or natural origin, with which the active compound is mixed or formulated to facilitate its application to the skin or hair or other object to be treated, or its storage, transport and/or handling. In general, any of the materials customarily employed in formulating pesticides, herbicides, or fungicides, are suitable. The inventive pesticidal compositions of the present invention may be employed alone or in the form of mixtures with such solid and/or liquid dispersible carrier vehicles and/or other known compatible active agents such as other pesticides, or pediculicides, acaricides, nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use. The pesticidal compositions of the present invention can be formulated or mixed with, if desired, conventional inert pesticide diluents or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, foams, pastes, tablets, aerosols, natural and synthetic materials impregnated with active compounds, microcapsules, and formulations used with burning equipment, such as fumigating cartridges, fumigating cans and fumigating coils, as well as ULV cold mist and warm mist formulations, etc.

Formulations containing the pesticidal compositions of the present invention may be prepared in any known manner, for instance by extending the pesticidal compositions with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. Suitable liquid diluents or carriers include water, petroleum distillates, or other liquid carriers with or without surface active agents. The choice of dispersing and emulsifying agents and the amount employed is dictated by the nature of the composition and the ability of the agent to facilitate the dispersion of the pesticidal compositions of the present invention. Non-ionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

Liquid concentrates may be prepared by dissolving a composition of the present invention with a solvent and dispersing the pesticidal compositions of the present inventions in water with the acid of suitable surface active emulsifying and dispersing agents. Examples of conventional carrier vehicles for this purpose include, but are not limited to, aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated especially chlorinated, aromatic hydrocarbons (e.g. chloro-benzenes, etc.), cycloalkanes, (e.g. cyclohexane, etc.). paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide etc.) sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers such as ground natural minerals (e.g. kaolins, clays, vermiculite, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.).

Surface-active agents, i.e., conventional carrier vehicle assistants, that may be employed with the present invention include, without limitation, emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc. and especially alkyl arylpolyglycol ethers, magnesium stearate, sodium oleate, etc.); and/or dispersing agents such as lignin, sulfite waste liquors, methyl cellulose, etc.

In the preparation of wettable powders, dust or granulated formulations, the active ingredient is dispersed in and on an appropriately divided carrier. In the formulation of the wettable powders the aforementioned dispersing agents as well as lignosulfonates can be included. Dusts are admixtures of the compositions with finely divided solids such as talc, attapulgite clay, kieselguhr, pyrophyllite, chalk, diatomaceous earth, vermiculite, calcium phosphates, calcium and magnesium carbonates, sulfur, flours, and other organic and inorganic solids which acts carriers for the pesticide. These finely divided solids preferably have an average particle size of less than about 50 microns. A typical dust formulation useful for controlling pests contains 1 part of pesticidal composition and 99 parts of diatomaceous earth or vermiculite. Granules may comprise porous or nonporous particles. The granule particles are relatively large, a diameter of about 400–2500 microns typically. The particles are either impregnated or coated with the inventive pesticidal compositions from solution. Granules generally contain 0.05–15%, preferably 0.5–5%, active ingredient as the pesticidally-effective amount. Thus, the contemplated are formulations with solid carriers or diluents such as bentonite, fullers earth, ground natural minerals, such as kaolins, clays, talc, chalk, quartz, attapulgite, montmorillonite or diatomaceous earth vermiculite, and ground synthetic minerals, such as highly-dispersed silicic acid, alumina and silicates, crushed and fractionated natural rocks such as calcite, marble, pumice, sepiolite and dolomite, as well as synthetic granules of inorganic and organic meals, and granules of organic materials such as sawdust, coconut shells, corn cobs and tobacco stalks. Adhesives, such as carboxymethyl cellulose, natural and synthetic polymers, (such as gum arabic, polyvinyl alcohol and polyvinyl acetate), and the like, may also be used in the formulations in the form of powders, granules or emulsifiable concentrations.

If desired, colorants such as inorganic pigments, for example, iron oxide, titanium oxide and Prussian Blue, and organic dyestuffs, such as alizarin dyestuffs, azo dyestuffs or metal phthalocyanine dyestuffs, and trace elements, such as salts of iron, manganese, boron, copper, cobalt, molybdenum and zinc may be used.

In commercial applications, the present invention encompasses carrier composition mixtures in which the pesticidal compositions are present in an amount substantially between about 0.01–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all formulations that comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

Furthermore, the present invention encompasses methods for killing, combating or controlling pests, which comprises applying to at least one of correspondingly (a) such pests and (b) the corresponding habitat thereof, i.e. the locus to be protected, e.g. to the head or body, a correspondingly combative, a pesticidally effective amount, or toxic amount of the particular pesticidal compositions of the invention alone or together with a carrier as noted above. The instant formulations or compositions may be applied in any suitable usual manner, for instance by shampooing, rubbing, spreading, spraying, atomizing, vaporizing, scattering, dusting, watering, squirting, sprinkling, pouring, fumigating, and the like. The method for controlling human body louse comprises applying the inventive composition, ordinarily in a formulation of one of the aforementioned types, to a locus or area to be protected from the human body louse, such as the hair or scalp. The compound, of course, is applied in an amount sufficient to effect the desired action. This dosage is dependent upon many factors, including the targeted pest, the carrier employed, the method and conditions of the application, whether the formulation is present at the locus in the form of a shampoo, hair gel, creme, or body lotion, an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of this invention at the locus to be protected—i.e., the dosage with which the pest comes in contact—is of the order of 0.001 to 5.0% based on the total weight of the formulation, though under some circumstances the effective concentration will be as little as 0.0001% or as much as 20%, on the same basis.

The pesticidal compositions and methods of the present invention are effective against different species of human body louse, including head lice, body lice and pubic lice, and it will be understood that the body lice exemplified and evaluated in the working Examples herein is representative of such a wider variety.

The composition and method of the present invention will be further illustrated in the following, non-limiting Examples. The Examples are illustrative of various embodiments only and do not limit the claimed invention regarding the materials, conditions, weight ratios, process parameters and the like recited herein.

EXAMPLE 1

The following aerosol formulations of the present invention may be prepared. The active ingredient included in the formulations herein comprise a neurally effective substance, a combination of neurally effective substances, or a combination of neurally effective substances and other diluents added for aesthetic purposes. It has been found that synergistic effects are produced with various combinations.

1. 3% active ingredient
    20% DME (Dimethyl ether)
    1.5% Propanol
    75.5% Isopar M
2. 1.5% active ingredient
    20.0% DME (Dimethyl ether)

1.5% Propanol
   77.0% Isopar M
3. 3.0% active ingredient
   3.5% $CO_2$ (Carbon dioxide)
   1.5% Propanol
   92.0% Isopar M
4. 1.5% active ingredient
   3.5% $CO_2$ (Carbon dioxide)
   1.5% Propanol
   93.5% Isopar M
5. Active ingredient: 1–7% by weight
   Solvent A: 50–94.1% by weight (any of the following)
     (a) Isopar H
     (b) Isopar L
     (c) Isopar M
   Solvent B: 0–10% by weight (any of the following)
     (a) d Limonene
     (b) Synthetic Solvents EE-195
     (c) Synthetic Solvents EE-216
     (d) Synthetic Solvents EE-235
   Propellant: 4.9%–18% by weight
     (a) Carbon dioxide
     (b) Propane
     (c) Propane-butane mixture The solvents and propellants may be any of the listed materials and/or combinations thereof and are not limited to those identified above. The materials identified have been found to be satisfactory.

$CO_2$ (carbon dioxide) and DME (dimethyl ether) are the preferred propellants used in the aerosol formulations, however other propellants known to those skilled in the art would be operative.

Propanol is used to make the active ingredient miscible with the Isopar M. Isopar M is not considered by EPA or the state of California as a VOC (volatile organic compound).

EXAMPLE 2

A typical liquid formulation is as follows:
Active insecticide: 1–5% by weight
Solvent A: 75–99% by weight
   (a) Isopar H
   (b) Isopar L
   (c) Isopar M
Solvent B: 0–20% by weight
   (a) d Limonene
   (b) Synthetic Solvents EE-195
   (c) Synthetic Solvents EE-216
   (d) Synthetic Solvents EE-235
Solvent C: 75–99% by weight
   (a) Soltrol 100

It is to be understood that the percentages set forth herein are approximations and can be varied within degrees by those skilled in the art and still attain effective results. Also, other substances may be used. The above-identified materials have been used satisfactorily. Soltrol 100 is a solvent of isoparaffinic hydrocarbons ($C_9$ through $C_{11}$) sold by Philips Chemical Co. The solvents listed may be used individually or in any combination.

A fragrance may be added if desired to enhance the marketing of the pesticide, especially for indoor use and for general retail markets. The pesticide may be used domestically, commercially, indoors, outdoors, for pets, nurseries, and agriculturally. The pesticide of the present invention has also been found to be useful for control of head lice on humans and as a repellent to be used on the skin of humans.

The resulting aerosol or liquid solvent formulations of the invention are compositions capable of directly invading the exoskeleton of most insects and arachnids. There are over one million species of common pests such as ants, roaches, fleas, termites, beetles, mites and spiders. All are potential targets.

Emulsifiable concentrate formulations are within the preview of this invention. These emulsifiable concentrates are particularly useful for outdoor application to plant foliage. These emulsifiable concentrates are easy to use; simply mix with water in the proper proportions and spray with conventional spray applicators. Emulsifiers and surfactants well known in the art can be used in preparing the emulsions which can penetrate plant material to aid in producing systemic action.

EXAMPLE 3

A study was conducted to determine the insecticidal activity of the present invention against commonly found insects such as German cockroaches, cat fleas and Argentine ants. As described the term "dust" is used for the insecticide in a dry crystalline powder form and the term "powder" is used for dry formulations that are intended to be mixed with water.

Tests With Cockroaches

Continuous exposure tests.—The intrinsic insecticidal activity of the insecticide dust against *B. germanica* was determined by exposing cockroaches to fresh and aged deposits of the dust. Replicated groups of three to ten adult cockroaches from culture were confined to deposits of the dust, and its speed of action in terms of knockdown (KD) and paralysis was determined. Adult male cockroaches from culture were placed directly onto fairly heavy deposits of dust (1 to 1.2 cc) spread evenly on filter paper in covered 9-cm-diameter petri dishes. The time for irreversible KD to occur (KT) was determined from periodic, irregular observation. The insects were considered KD when they were on their back, or could be turned over, and could not right themselves within at least two minutes. KT-50 and KT-90 values (time for 50% and 90% KD, respectively) were calculated by interpolation of KD between times when data was collected; average KT value were obtained from the individual KD data. Comparison of KD activity was made with some commercial dust formulations including a non-fluorinated silica aerogel (SG-68), Drione™ (a fluorinated silica aerogel+pyrethrins), and a commercial diatomaceous earth (Celite™) applied and tested in the same manner.

The effects of atmospheric moisture and deposit age on the efficacy of the present insecticide dust were determined by the speed of action (KT) on cockroaches confined to deposits of the dust aged and tested at 98% (high) and 58% (moderate) relative humidity (RH). Average KT values were determined for fresh dust and for dust aged 2 weeks and 4 weeks. Cockroaches were exposed to 1 cc of dust in petri dishes, as described previously. Eighteen-mesh window screen covers on the dishes allowed for maintenance of the proper humidity and kept cockroaches from escaping from the damp dusts. For these tests dishes of dust were aged and tested on a wire mesh platform in saran-sealed aquaria. Enough dishes were prepared so that each deposit was tested only once. Water below the platform was used to maintain 98% RH, and a saturated aqueous sodium bromide solution was used to maintain 58% RH.

Choice box tests.—The activity and repellency of the present insecticide dust in a choice test was determined with standard two-compartment choice boxes.

Choice boxes are 30.5 cm square, 10 cm tall wooden boxes, with a tempered masonite floor. A vertical partition panel separates the box into two equal-sized compartments. A 1.3 cm hole at the top center of the partition panel allows cockroaches to move from one compartment to the other. Transparent sheet plexiglass (0.3 cm thick) taped to the top retains cockroaches in the box and allows observation of live and dead in each compartment. A piece of masonite keeps one compartment dark (dark compartment). The other compartment (light compartment) is exposed to normal room light conditions.

Five boxes were used for each treatment and the untreated control. For these tests 10 cc of test dust was spread evenly over the floor of the dark compartment and 20 adult male *B. germanica* were released into the light compartment, where there was food and water. A cork in the partition hole was removed two hours later, when the cockroaches settled. Cockroaches prefer to aggregate in the dark, and they will normally readily move from the light compartment to the dark compartment of untreated choice boxes within a day or two. Once the partition cork was removed, the insects could move from the light compartment into treated dark compartment. The number dead and alive in each compartment of each box was recorded every few days. It was presumed that mortality was produced by contact with the insecticide in the dark, regardless of where the insects eventually died. Reluctance to move into the dark is attributable to the repellency of the treatment. Repellent treatments usually result in increased survivorship in the light compartment.

The mortality produced in choice boxes, and the position of cockroaches in relation to the treatment, provides a measure of the likely ultimate efficacy of a treatment when used under actual field conditions. In choice box tests, cockroaches are given an opportunity to encounter or avoid insecticide deposits. Highly toxic deposits may be ineffectual if cockroaches sense their presence and avoid lethal contact with them. On the other hand, slow-acting insecticides such as boric acid are effective in choice box tests because cockroaches readily walk on those deposits and are eventually killed by them.

Tests with Cat Fleas

Adult cat fleas, cultured under laboratory conditions were used in the study. Eggs collected from caged cats were reared through the larval period to adulthood on a special blood media. Adults used in the tests were approximately 2 to 3 days old (i.e., 2 to 3 days post-eclosion from the cocoon stage).

Speed of action of minimal deposits.—The rate of knockdown of fleas exposed to filter paper treated with the present insecticide dust and SG-68 silica aerogel was determined. Strips of No. 1 Whatman filter paper measuring 2 cm by 15 cm were submerged in the dusts and the excess shaken off. The lightly dusted strips were slipped into 2.5 cm- diameter by 15 cm tall glass test tubes and groups of fleas were directed from rearing emergence jars into the tubes. The open end of the tube was covered with parafilm. The tubes were left in a vertical position in a test tube rack. Because such a small amount of dust was used, all of it adhered to the paper and none could be seen on the surface of the test tubes. The fleas contacted the dust when they walked on the paper. Exposure to the dust was ensured because live fleas prefer the paper surface to the smooth surface of the test tube. Knockdown of fleas in the tubes was observed and recorded every few minutes until all the fleas were down. The fleas were considered KD if they were paralyzed at the bottom of the tube. Rate of KD (KT) was interpolated from the number of fleas KD at each time of observation.

Exposures on dusted carpet.—The minimum lethal dose and potential effectiveness of the present insecticide dust against fleas indoors was determined by exposing aliquots of fleas to a series of decreasing dosages of the dust on carpet. Dri-Die™ SG-68, a sorptive desiccant silica aerogel, was used as a comparative standard.

Weighed amounts of dust were sifted as evenly as possible onto the surface of 9-cm-diameter disks of new shag carpet at the bottom of 9 cm by 45-cm-tall plastic cylinders. The carpet was made of 100% nylon fibers and a jute backing. It has 9 double-stranded loops per $cm^2$, each strand being about 1.6 cm long.

The highest rate of dust applied was 1.2 cc/disk [14.2 $cc/929cm^2$; that rate was successively halved and tested to the lowest rate of 0.06 $cc/929cm^2$ (i.e., 9 rates tested)]. For exposure on each treatment rate, fleas from eclosion jars were directed onto the carpet, where they were confined for 24 hours. One or two replicates of 12 to 20 fleas were used for most rates, but 3 replicates were used for some rates. Because fleas cannot climb on the plastic or jump high enough to escape, they remained in contact with the carpet at the bottom of the cylinder. Untreated disks served as controls. Tests were conducted under ambient laboratory conditions (approximately 74° F. and 45% RH) and in an incubator cabinet at 98% RH.

The efficacy of the dust treatments was determined from the percentage of fleas that died within a 24-hour exposure period. Live and dead fleas on each disk were counted after tapping all the fleas from a disk into a basin of cool water. Live fleas move and swim vigorously. Fleas were considered dead if they sank, were immobile, or if they only had feeble, barely perceptible movement of their appendages.

Effect of humidity and volatility.—The specific application rate of 1.8 $cc/929cm^2$ was used to compare the activity and volatility of the "active ingredient" in the present insecticide dust and some other dusts at ambient and 98% RH. Using the method described above, mortality at 24 hours was determined for fleas exposed to fresh insecticide, insecticide baked 48 hours at 250° F., diatomaceous earth, and silica aerogel. It was presumed that high temperature might drive off volatile actives, and that abrasive diatomaceous earth or sorptive non-fluorinated silica gel would provide greater kill at low humidity than at high humidity. Differences between rates of kill may indicate the mode of action of the insecticide dust.

Tests with Argentine Ants

Based on the results obtained with the present insecticide in tests against cockroaches and fleas, Argentine ants were exposed to selected low doses of the dust as well as to comparative doses of SG-68 desiccant. Worker ants collected from a citrus grove were aspirated for study approximately 30 minutes before the test began. Aliquots of ants (11–15 for each of three replicates per treatment) were dumped onto lightweight deposits of the present insecticide dust and SG-68 spread evenly over the surface of filter paper waxed into the floor of 9-cm diameter glass petri dishes. Knockdown of the ants was observed every 5 minutes until all the ants in the treatments were down. An untreated set of papers served as a control series. The exposure tests provided an indication of the relative speed of action of the present insecticide and the SG-68 dusts against this species.

Results And Discussion

An embodiment of the present invention mixes an alkaline earth metal carbonate, such as calcium carbonate, an alkali metal bicarbonate, such as sodium bicarbonate, at least one neurally effective substance, and an absorbent material, such as diatomaceous earth. In addition, inert ingredients such as silica gel and a scenting agent may be added as desired in varying amounts for color and texture. Aside from the scenting agent, all of the above-mentioned ingredients are preferably mixed in powdered form.

The relative concentrations of the mixture are preferably about 30%–35% alkaline earth carbonate, 60%–65% alkali metal carbonate, 1%–2% neurally effective substance, and 4$–5% absorbent material (all by weight). However, the individual constituents may vary within the following ranges while still achieving the desired result: 5%–91% alkaline earth carbonate, 6%–95% alkali metal carbonate, 1%–93% neurally effective, and up to 90% absorbent material (all by weight). The mix is ground to a powder, preferably having a granular size of less than 100 microns.

The irreversible knockdown (KD) of cockroaches exposed to fresh and aged deposits of this embodiment the present insecticide at moderate and high humidities is summarized in Table 1.

TABLE 1

Knockdown of adult male German cockroaches confined to dust deposits aged and tested at high (98%) and moderate (58%) humidity.

| Treatment[a] | | Avg. hours for KD on deposits of indicated age | | | | | |
|---|---|---|---|---|---|---|---|
| | | Fresh | | 2 Weeks | | 4 Weeks | |
| RH | | KT-50 | KT-90 | KT-50 | KT-90 | KT-50 | KD-90 |
| Present insecticide | 58% | 0.3 | 0.6 | 0.3 | 0.7 | 0.3 | 0.7 |
| Silica gel | | 6.1 | 16.0 | 4.3 | 5.8 | 7.4 | 18.4 |
| Celite | | (39%)[b] | | (6%) | | (42%) | |
| Untreated | | (0%) | | (0%) | | (16%) | |
| Present insecticide | 98% | 0.3 | 0.5 | 0.6 | 1.2 | 0.7 | 1.3 |
| Silica gel | | 6.7 | 12.3 | 8.3 | 17.3 | 13.3 | 21.9 |
| Celite | | (4%) | | (0%) | | (16%) | |
| Untreated | | (0%) | | (0%) | | (13%) | |

[a]1 cc/9-cm-diam petri dish. Five replicates each with 10 cockroaches, were used for each exposure. Dusts spread onto Whatman No. 1 filter paper. Silica gel was SG-68 silica aerogel, an aerogel containing no fluoride. Celite is a commercial diatomaceous earth filter aid (Manville, Hyflo ™).
[b]Numbers in parentheses indicate total % KD at 24 hours, in instances where average KT-50 was not achieved.

The present insecticide dust provided rapid KD of German cockroaches, the average KT-50 being about 18 minutes, and 100% being down within about 40 minutes. Neither high humidity nor aging up to 4 weeks had a deleterious effect on its speed of action against cockroaches. Because even the most rapid-action desiccants require>30 minutes for KD, the effect observed with present insecticide suggests that the toxic action of the dust was not attributable solely to a sorptive ingredient. The affected cockroaches had curled or distended abdomens, and looked to be paralyzed as when toxified by a nervous system insecticide.

As expected, the non-fluorinated SG-68 desiccant took several hours to kill cockroaches, and was slightly less effective at high humidity. Typically, the desiccated cockroaches died standing upright, and did not show signs of tremors or paralysis.

Diatomaceous earth (like Celite™) alone is not usually considered to be an effective insecticide. Being an abrasive, the toxic action of diatomaceous earth occurs as a result of dusted insects slowly losing body water through abraded cuticle. Because moist air has little evaporative power, Celite™ was even less effective at high humidity.

Choice box tests with cockroaches.—Although the present insecticide dust provided rapid kill in continuous exposure tests, there was significant survivorship in the choice tests. There is usually a direct relationship between the speed of action of an insecticide and its repellency, and this relationship appears to have been confirmed in the choice box study. As shown in Table 5, deposits of the present insecticide dust provided mediocre kill of cockroaches in choice boxes, with 52% of the cockroaches being alive at 7 days and 40% alive at 14 days. Boric acid dust, on the other hand, provided 98% kill of cockroaches within a week.

Table 2 also shows that a high percentage of the live cockroaches in choice boxes treated with the present insecticide were always in the less-preferred light compartment, away from the dust. This was not so with boric acid, a non-repellent insecticide. Avoidance of the dust by survivors is characteristic of repellent insecticides such as silica gels (repellent by nature of their small particle size and sorptive properties) and fast-knockdown toxicants such as pyrethrins and pyrethroids.

TABLE 2

Activity and repellency of fresh dust deposits against German cockroaches, as measured in choice boxes.

| Dust[a] | % Mortality on day | | | % of live in light on day | | | Days for KD[b] | |
|---|---|---|---|---|---|---|---|---|
| | 1 | 7 | 14 | 1 | 7 | 14 | KT-50 | KT-90 |
| Present insecticide | 25 | 48 | 60 | 84 | 100 | 100 | 7.7 | — |
| Boric acid, tech. | 0 | 98 | 100 | 13 | 100 | — | 4.0 | 5.7 |
| Untreated | 0 | 3 | 10 | 12 | 3 | 18 | — | — |

[a]10 cc dust spread evenly over floor of dark compartment. For each dust, 3 replicates were tested, each with 20 adult male B. germanica.
[b]KT-50 and KT-90 are average days for 50% and 90% of the cockroaches to be irreversibly knocked down (KD).

The present insecticide dust, therefore, had high intrinsic insecticidal action against cockroaches, it had excellent activity at high and low humidity, and it retained activity for at least a month. The dust was, however, somewhat repellent, resulting in a high percentage of cockroaches surviving in choice tests. Direct application to cockroaches would certainly kill them.

Speed of action and minimum effective dose against fleas.—A low dose of the present insecticide dust provided very rapid knockdown of adult fleas. On paper in tubes it took nearly 4 hours for 90% knockdown of fleas on SG-68 silica gel, but less than 5 minutes for knockdown on the present insecticide. As with cockroaches, this rapid action suggests the presence of a nerve-involving insecticide rather than an adsorptive desiccant or an abrasive.

The good activity against fleas at a low dose was substantiated in the series of exposure tests with successively lower doses of the present insecticide on carpet. As shown in Table 3, complete kill of fleas was achieved with as little as 0.2 cc/929 cm$^2$ of the present invention. Lower doses were not effective.

TABLE 3

Minimum effective dosages of fresh dust deposits on carpet against adult cat fleas, *Cunocephalides felis*.

| | % Mortality of fleas at 24 hours[a] | | | |
|---|---|---|---|---|
| Rate | Present insecticide | | Silica gel (SG-68) | |
| (cc/929 cm$^2$)[b] | Ambient RH | 98% RH | Ambient RH | 98% RH |
| 14.2 | 100 | 100 | 100 | 100 |
| 7.1 | 100 | 100 | 100 | 100 |
| 3.6 | 100 | 100 | 100 | 100 |
| 1.8 | 100 | 93.6 | 100 | 92.3 |
| 0.9 | 100 | 100 | 100 | 100 |
| 0.4 | 100 | 77.8 | 100 | 42.9 |
| 0.2 | 100 | 81.8 | 100 | 46.7 |
| 0.1 | 23.5 | — | 100 | — |
| 0.06 | 4.1 | — | 1.8 | — |
| Untreated | 9.7 | 11.3 | — | — |

[a]% mortality of treatments corrected with Abbott's formula to account for control mortality.
[b]Rates extrapolated from volume amounts applied to 78.5 cm$^2$ carpet discs. Highest rate applied (14.2 cc/929 cm$^2$) is equivalent to 1.2 cc/disc; other rates are proportional.

High humidity appeared to reduce the effectiveness of the dust at low rates of application as shown in Table 4.

TABLE 4

Effect of humidity on the activity of a low dose of dust deposit against adult cat fleas.

| | % Mortality at indicated RH[a] | |
|---|---|---|
| Dust treatment | Ambient | 98% |
| Present insecticide | 100 | 93.6 |
| Present insecticide (baked)[b] | 72.7 | 2.8 |
| Celite | 21.4 | 23.1 |
| Silica gel | 100 | 92.3 |
| Untreated | 5.6 | 6.4 |

[a]Fresh powders (1.8 cc/929 cm$^2$) applied to carpet. Fifteen to 20 fleas confined to treatments 24 hours. One to 2 replicates per treatment. Ambient humidity 25–40% RH.
[b]Heated 48 hours in hot-air oven at 250° F.

Surprisingly, the SG-68 also provided good kill at approximately the same low rates. Since SG-68 is a non-toxic desiccant, it could have been concluded erroneously that the present insecticide dust also killed fleas by desiccating them. The much more rapid action found in the test tube assay suggests that there is a toxic component in the present insecticide formulation. The toxic component appears to involve toxification of the insect's nerves or cells.

Activity of the present insecticide against Argentine ants.—The rapid activity of the present insecticide against Argentine ants is shown in Table 5.

TABLE 5

Activity of minimal dust deposits against the Argentine ant, *Iridomyrmex humilis*.

| Dust | Rate (cc/929 cm$^2$) | % Dead at minutes of exposure | | | | | | Time for KD (min) | |
|---|---|---|---|---|---|---|---|---|---|
| | | 5 | 10 | 20 | 40 | 60 | 80 | KT-50 | KT-90 |
| Present Insecticide | 0.2 | 36 | 100 | | | | | 6.0 | 9.2 |
| | <0.06 | 23 | 32 | 100 | | | | 11.2 | 14.2 |
| SG-68 | 0.2 | 0 | 0 | 0 | 23 | 66 | 89 | 55.9 | 75.7 |
| | <0.06 | 0 | 0 | 0 | 24 | 84 | 100 | 49.5 | 60.3 |
| Untreated | — | 0 | 0 | 0 | 0 | 7 | 7 | — | — |

[a]Mortality based on 3 replicates, each with 11–15 worker ants.

The lightweight deposit (0.2 cc/929 cm$^2$) knocked down all the ants in less than 10 minutes; and an extremely light deposit (<0.06 cc/929 cm$^2$) provided effects that were nearly as rapid. The latter deposit was achieved by brushing a small amount of the dust onto the paper, and then tapping the remnant dust off the paper as the dish was inverted. Only a very small amount of dust remained. The SG-68 desiccant had a somewhat slower effect, resulting in high levels of KD within about 50 to 75 minutes. Desiccants such as SG-68 are active against ants such as these, perhaps because this ant has a relatively low percentage body water (<70%) and a large surface area compared to its body volume, a combination of which allows for rapid water loss from this insect.

As with the exposures of cockroaches and fleas, the ants contacting the present insecticide dust exhibited classic symptoms of neural toxication. Ants contacting the dust were quickly paralyzed. There was rapid running and apparent irritation before the onset of paralysis, a symptom often observed with ants exposed to finely divided dusts and fast-acting insecticides. There appeared to be less irritation among ants exposed to SG-68.

As with all dust formulations, care should be exercised to minimize airborne particulates of the dust at the time of application or afterwards. This may be more important if the dust is applied to carpet or furnishings for controlling fleas than if applied along baseboards, under appliances, or in other similar places for controlling cockroaches or ants.

The presence of a volatile active component in the present insecticide formulation was preliminarily verified when the activity of fresh insecticide was compared to that of heated (i.e., baked) insecticide. As shown in Table 4, the present insecticide baked 48 hours at 250° F. was less effective against fleas, and was significantly less effective when tested at high humidity. Baking apparently removed volatile active components or altered the configuration of the dust diluent. That removal or alteration reduced activity. Baking at higher temperature may reduce performance even more. Pyrethins and other botanical insecticides volatilize at 250° F., but can reportedly be more quickly and thoroughly removed at 350° F.

The effectiveness compares favorably to conventional pesticides, yet the above-described product is primarily inorganic and completely non-hazardous to humans and other animals.

An improved embodiment of the present invention using the neurally effective substances with the inorganic dust was prepared and tested as described below.

A control test was conducted using only the solid components of the embodiment. As summarized in Table 6, the least active dust substance was calcium carbonate, (CaCO$_3$). Only 10% of the cockroaches exposed to deposits of CaCO$_3$ were KD within 24 hours. The activity of CaCO$_3$ was not statistically different from the untreated control, and was the most inert of the ingredients tested. Amorphous silica (HiSil (R)233 marketed by Harwick, Akron, Ohio has been used satisfactorily), on the other hand, is a potent desiccant and was the most active of the dry ingredients, it's average KT$_{90}$ being 6.7 hours. The addition of amorphous silica to CaCO$_3$ proportionately increased the activity of the CaCO$_3$ obviously because of the sorptive qualities of the amorphous silica. As expected, diatomaceous earth and sodium bicarbonate were not highly insecticidal but they did provide significant KD within 24 hours. These data suggested that calcium carbonate was a suitable inert ingredient with which to determine the relative effects attributable to the neurally effective substances. CaCO$_3$ was used as an inert carrier or diluent in further tests to determine mechanisms of insecticidal action as described hereinafter.

TABLE 6

Average hours (± standard deviation) for 50% and 90% knockdown of adult male German cockroaches, Blattella, germanica, continuously confined to dust deposits.

| Dust or dust mix | KT$_{50}$ | | KT$_{90}$ | |
|---|---|---|---|---|
| | Hours | SD | Hours | SD |
| Calcium carbonate (CaCO$_3$) | — | — | (10% KD at 24 h) | |
| Amorphous silica (AS) | 4.9 | 0.38 | 6.7 | 1.38 |
| Diatomaceous Earth (DE) | 11.8 | 1.44 | 16.8 | 3.03 |
| Sodium bicarbonate (NaHCO$_3$) | 16.5 | 0.48 | 20.9 | 0.10 |
| CaCO$_3$ + 30% AS | 6.5 | 1.00 | 9.3 | 1.53 |
| CaCO$_3$ + 30% AS + 5% DE | 6.3 | 1.19 | 10.8 | 3.70 |
| CaCO$_3$ + 36% NaHCO$_3$ | 19.5 | 0.50 | (80% KD at 24 h) | |
| CaCO$_3$ + 5% AS | 13.7 | 3.44 | 19.4 | 1.52 |
| Untreated control | — | — | (0% KD at 24 h) | |

Average values based on 3 replicates, each with 10 cockroaches.
SD = standard deviation.
Exposures at 76° F., 55% relative humidity.

The pesticidal activity of the neurally effective substances combined only with CaCO$_3$ was determined. Each respective neurally effective substance was formulated at 5% (wt/wt) in CaCO$_3$ and cockroaches were confined to the mixture as described above for exposures to the dry dust ingredients. Weighed quantities of compound were added to CaCO$_3$ and the mix was thoroughly stirred in 500 ml glass beakers and then shaken with glass boiling beads in a capped specimen jar. The beads were screened out of the resultant mix. Exactly 1.2 cc of dust or dust was spread onto Whatman filter paper in 9-cm-diam petri dishes and the knockdown (KD) of cockroaches confined to the dust mix was determined by periodically observing KD.

The insecticidal activity of the neurally effective substances is summarized in Table 7. Again, CaCO$_3$ was not insecticidal and both sodium bicarbonate and diatomaceous earth provided comparatively slow KD. The most active neurally effective substances were benzyl acetate, phenyl ethyl alcohol, and terpineol. Each of these substances provided 90% KD of cockroaches in about one hour or so. Amyl cinnamic aldehyde was much slower, about as active as diatomaceous earth. Diethyl phthalate and dipropylene glycol may impart some favorable odor characteristics but they were not insecticidal. The complete dust embodiment of the present invention as described herein provided fastest KD, the KT$_{90}$ for it being only about 0.5 hours.

TABLE 7

Average hours (± standard deviation) for 50% and 90% knockdown of German cockroaches continuously confined to calcium carbonate + 5% ingredients of neurally effective substance.

| Dust or dust mix | KT$_{50}$ | | KT$_{90}$ | |
|---|---|---|---|---|
| | Hours | ±SD | Hours | ±SD |
| Calcium carbonate (dust) | — | — | (1.3% KD at 24 h) | |
| Sodium bicarbonate (dust) | 9.7 | 0.48 | 16.0 | 1.88 |
| Diatomaceous Earth (dust) | 9.4 | 0.00 | 15.5 | 0.00 |
| Amyl cinnamic aldehyde, 5% | 9.4 | 0.00 | 15.5 | 0.00 |
| Benzyl acetate | 0.7 | 0.05 | 1.0 | 0.18 |
| Diethyl phthalate | — | — | (0% KD at 18 h) | |
| Phenyl ethyl alcohol | 0.7 | 0.09 | 1.0 | 0.25 |
| Dipropylene glycol | — | — | (23% KD at 18 h) | |
| Terpineol | 0.7 | 0.08 | 1.1 | 0.17 |
| Dust embodiment* | 0.2 | 0.06 | 0.5 | 0.03 |

Average values based on 3 replicates, each with 10 cockroaches.
SD = standard deviation.
Exposures in laboratory at 78 ± 4° F., 55 ± 6% rh.
*The dust embodiment of the present invention contains benzyl acetate, terpineol and phenyl ethyl alcohol.

The above exposure trials with cockroaches indicate that the rapid pesticidal action of the formulation of the present invention is due to the neurally effective substance, not to any of the powdered components, either individually or combined.

A further test was conducted to compare the effectiveness of phenol vs. terpineol as a neurally effective substance. The respective substances were mixed with calcium carbonate at a range of wt/wt mixes. The preparations were tested using German cockroaches with the results provided in Table 8.

TABLE 8

Average hours for 50% and 90% knockdown of German cockroaches continuously confined to calcium carbonate + ingredients of phenol and terpineol

| Dust | % (wt/wt) | KT-50 (h) | KT-90 (h) |
|---|---|---|---|
| Phenol | 5.0 | <0.1 | 0.1 |
| | 2.5 | 0.2 | 0.4 |
| | 1.25 | 0.4 | 1.5 |
| | 0.63 | 7.5 | 20.3 |
| | 0.32 | 16.5 | 24.0 |
| Terpineol | 5.0 | 0.6 | 0.9 |
| | 2.5 | 9.4 | 20.6 |
| | 1.25 | 11.4 | 23.5 |
| | 0.63 | 14.7 | 22.1 |

Phenol was more insecticidal than terpineol. It is also much more toxic to humans and other mammals than are the other neurally effective substances tested. Cockroaches killed in the phenol mix turned black. At every rate tested, phenol provided faster KD. The minimum active dose for fresh phenol in CaCO$_3$ was approximately between 1.25% and 0.63%. The minimum active dose for fresh terpineol was above 2.5%. This assay confirms the theory as discussed below that speed of insecticidal activity of the neurally effective substances may be associated with the complexity and isomeric configuration of hydroxyl attachments to a six member carbon ring.

Having now fully set forth a detailed example and certain modifications incorporating the concept underlying the present invention, various other modifications will obviously occur to those skilled in the art upon becoming familiar with said underlying concept. It is to be understood, therefore, that within the scope of the appended claims, the invention may be practiced otherwise than as specifically set forth herein.

The mode of action of the neurally effective substances disclosed herein is not known. Each of the substances is considered to be non-toxic by the U.S. Food and Drug Administration and are frequently used in food and food additives. The applicants are unaware of pesticidal activity reported or ascribed to the neurally effective compounds as specifically taught herein.

It is proposed that in biology, the body's receptacles have an affinity for hydroxyl compounds, and are absorbed into the nerve endings, creating a genomic effect, which is highly desirable in a mode of action context. The more distal from the six member carbon ring that the hydroxyl is, the less likely it is that the body can metabolize this compound to the point that the hydroxyl can attach itself to the receptacle. Separation of the hydroxyl group from the ring by a chain of up to four (4) carbon atoms results in a corresponding decrease in activity. In general, carbon chains of five (5) or greater are usually inactive.

There is credible evidence that this in fact takes place, based on theories that estrogen and other pharmeuticals work in this manner. It is further postulated that the esters such as benzyl acetate are active because the body hydrolyzes the ester, enabling the hydroxyl group to become available for interaction with the body's receptacles. However, applicants do not wish to be bound by any specific theory of operation.

EXAMPLE 4

An unscented aerosol pesticide composition (Eco PCO ACU (ADL-2-12-A), EcoSmart Technologies, Inc.) comprising neurally active benzyl alcohol was made. The unscented composition contained:

| | |
|---|---|
| 10% | Arylessence AA029661 (which contains Benzyl Alcohol (88.04%), Tetrahydrofurfuryl Alcohol (10.87%) and Phenethyl Propionate 1.09%) |
| 4% | Isopropyl Alcohol |
| 71.9% | Isopar M, and |
| 14% | Propellant A-108. |

The compositions were evaluated as to their effectiveness in the control of the following target pests: Southern fire ant, Argentine ant, Carpenter ant, Cat flea, European earwig, Brown dog tick, Carpet beetle, House fly, Field cricket, American cockroach, German cockroach, Paper wasp, Western subterranean termite, Southern house mosquito, Pillbug, Long-bodied cellar spider, and Wolf spider. A scented aerosol composition (Eco PCO AC (ADL-2-12-B), EcoSmart Technologies, Inc.) was also tested as a positive control. Sprays of the compositions were all directed at the target pest and the surrounding substrate, and mortality was assessed at varying time periods. The testing protocols and results are set forth below in Examples 5.

EXAMPLE 5

Southern Fire Ant, *Solenopsis xyloni*

| | |
|---|---|
| Life Stage: | Adult workers |
| Experimental Design: | Randomized Complete Block Design |
| Replication: | 4 |
| # Organisms per Replicate: | 10 |

Holding Conditions: Southern fire ants were field collected in Fresno County, Calif. The ants were held for about 2 hours prior to study initiation. The ants were then transferred into clear plastic cups (7.5 cm high×11 cm dia) and held at 70° F. The cup lids were removed during the test. A circular disc of vinyl flooring was placed in the bottom of each cup, and the ants moved freely over the floor surface. No food or water was provided.

Spray Application: A short burst of the unscented pesticidal composition, or the positive control pesticidal composition was directed at the test insects. No spray was applied to the untreated control. The spray canister was held 30 cm from the target. Complete spray coverage of the insects and floor surface was observed. The amount of product dispensed was determined by weighing the canister before and after each spray (Table 1).

Evaluation: The number of dead ants was assessed at 1, 5, and 10 minutes and at 1, 24, and 48 hours posttreatment. Death was defined as the inability of the organism to move when probed.

Results and Discussion: The ants became agitated immediately upon being sprayed with the test products. At 1 minute posttreatment 87.5% of the ants were dead in the treatment of Eco PCO ACU (ADL-2-1 2-A), compared to 67.5% in the treatment with Eco PCO AC (ADL-2-12-B) (Table 2). All sprayed ants were dead within 5 minutes, and complete survival was observed in the untreated group.

TABLE 1

Amount of product (grams) dispensed at each spray application - Southern fire ant.

| | Replicate | | | | |
|---|---|---|---|---|---|
| Treatment | 1 | 2 | 3 | 4 | Mean |
| Eco PCO ACU (ADL-2-12-A) | 1.0 | 0.5 | 1.2 | 0.7 | 0.9 |
| Eco PCO AC (ADL-2-12-B) | 0.6 | 0.5 | 0.3 | 0.9 | 0.6 |
| Untreated | 0.0 | 0.0 | 0.0 | 0.0 | 0.0 |

TABLE 2

Number of dead southern fire ants (% mortality) n = 10 at
1, 5, and 10 minutes and 1, 24, and 48 hours posttreatment.

| Treatment | Posttreatment Time | Replicate 1 | 2 | 3 | 4 | Mean |
|---|---|---|---|---|---|---|
| Eco PCO ACU (ADL-2-12-A) | 1 min. | 7 (70.0) | 8 (80.0) | 10 (100.0) | 10 (100.0) | 8 (87.5) |
| | 5 min. | 10 (100.0) | 10 (100.0) | 10 (100.0) | 10 (100.0) | 10 (100.0) |
| | 10 min. | 10 (100.0) | 10 (100.0) | 10 (100.0) | 10 (100.0) | 10 (100.0) |
| | 1 hr. | 10 (100.0) | 10 (100.0) | 10 (100.0) | 10 (100.0) | 10 (100.0) |
| | 24 hrs. | 10 (100.0) | 10 (100.0) | 10 (100.0) | 10 (100.0) | 10 (100.0) |
| | 48 hrs. | 10 (100.0) | 10 (100.0) | 10 (100.0) | 10 (100.0) | 10 (100.0) |
| Eco PCO AC (ADL-2-12-B) | 1 min. | 8 (80.0) | 7 (70.0) | 6 (60.0) | 6 (60.0) | 6 (67.5) |
| | 5 min. | 10 (100.0) | 10 (100.0) | 10 (100.0) | 10 (100.0) | 10 (100.0) |
| | 10 min. | 10 (100.0) | 10 (100.0) | 10 (100.0) | 10 (100.0) | 10 (100.0) |
| | 1 hr. | 10 (100.0) | 10 (100.0) | 10 (100.0) | 10 (100.0) | 10 (100.0) |
| | 24 hrs. | 10 (100.0) | 10 (100.0) | 10 (100.0) | 10 (100.0) | 10 (100.0) |
| | 48 hrs. | 10 (100.0) | 10 (100.0) | 10 (100.0) | 10 (100.0) | 10 (100.0) |
| Untreated | 1 min. | 0 (0.0) | 0 (0.0) | 0 (0.0) | 0 (0.0) | 0 (0.0) |
| | 5 min. | 0 (0.0) | 0 (0.0) | 0 (0.0) | 0 (0.0) | 0 (0.0) |
| | 10 min. | 0 (0.0) | 0 (0.0) | 0 (0.0) | 0 (0.0) | 0 (0.0) |
| | 1 hr. | 0 (0.0) | 0 (0.0) | 0 (0.0) | 0 (0.0) | 0 (0.0) |
| | 24 hrs. | 0 (0.0) | 0 (0.0) | 0 (0.0) | 0 (0.0) | 0 (0.0) |
| | 48 hrs. | 0 (0.0) | 0 (0.0) | 0 (0.0) | 0 (0.0) | 0 (0.0) |

EXAMPLE 6

Argentine Ant, *Iridomyrmex humilis*

| | |
|---|---|
| Life Stage: | Adult workers |
| Experimental Design: | Randomized Complete Block Design |
| Replication: | 4 |
| # Organisms per Replicate: | 10 |

Holding Conditions: Argentine ants were field collected in Fresno County, Calif. The ants were held for about 2 hours prior to study initiation. The ants were then transferred into clear plastic cups (7.5 cm high×11 cm dia) and held at 70° F. The cup lids were removed during the test. A circular disc of vinyl flooring was placed in the bottom of each cup, and the ants moved freely over the floor surface. No food or water was provided.

Spray Application: A short burst of the unscented pesticidal composition, or the positive control pesticidal composition was directed at the test insects. No spray was applied to the untreated control. The spray canister was held 30 cm from the target. Complete spray coverage of the insects and floor surface was observed. The amount of product dispensed was determined by weighing the canister before and after each spray (Table 1).

Evaluation: The number of dead ants was assessed at 1, 5, and 10 minutes and at 1, 24, and 48 hours posttreatment. Death was defined as the inability of the organism to move when probed.

Results and Discussion: The ants became agitated immediately upon being sprayed with the test products. At 1 minute posttreatment 100% of the ants were dead in the Eco PCO ACU (ADL-2-12-A) and Eco PCO AC (ADL-2-12-B) treatments (Table 2). Complete survival was observed in the untreated group.

TABLE 1

Amount of product (grams) dispensed at each spray application-Argentine ant.

| Treatment | Replicate 1 | 2 | 3 | 4 | Mean |
|---|---|---|---|---|---|
| Eco PCO ACU (ADL-2-12-A) | 0.8 | 1.6 | 1.1 | 1.1 | 1.2 |
| Eco PCO AC (ADL-2-12-B) | 0.9 | 1.2 | 0.8 | 0.5 | 0.9 |
| Untreated | 0.0 | 0.0 | 0.0 | 0.0 | 0.0 |

TABLE 2

Number of dead Argentine ants (% mortality) n = 10 at
1, 5, and 10 minutes and 1, 24, and 48 hours posttreatment.

| Treatment | Posttreatment Time | Replicate 1 | 2 | 3 | 4 | Mean |
|---|---|---|---|---|---|---|
| Eco PCO ACU (ADL-2-12-A) | 1 min. | 10 (100.0) | 10 (100.0) | 10 (100.0) | 10 (100.0) | 10 (100.0) |
| | 5 min. | 10 (100.0) | 10 (100.0) | 10 (100.0) | 10 (100.0) | 10 (100.0) |
| | 10 min. | 10 (100.0) | 10 (100.0) | 10 (100.0) | 10 (100.0) | 10 (100.0) |
| | 1 hr. | 10 (100.0) | 10 (100.0) | 10 (100.0) | 10 (100.0) | 10 (100.0) |
| | 24 hrs. | 10 (100.0) | 10 (100.0) | 10 (100.0) | 10 (100.0) | 10 (100.0) |
| | 48 hrs. | 10 (100.0) | 10 (100.0) | 10 (100.0) | 10 (100.0) | 10 (100.0) |

TABLE 2-continued

Number of dead Argentine ants (% mortality) n = 10 at
1, 5, and 10 minutes and 1, 24, and 48 hours posttreatment.

| Treatment | Posttreatment Time | Replicate 1 | 2 | 3 | 4 | Mean |
|---|---|---|---|---|---|---|
| Eco PCO AC | 1 min. | 10 (100.0) | 10 (100.0) | 10 (100.0) | 10 (100.0) | 10 (100.0) |
| (ADL-2-12-B) | 5 min. | 10 (100.0) | 10 (100.0) | 10 (100.0) | 10 (100.0) | 10 (100.0) |
| | 10 min. | 10 (100.0) | 10 (100.0) | 10 (100.0) | 10 (100.0) | 10 (100.0) |
| | 1 hr. | 10 (100.0) | 10 (100.0) | 10 (100.0) | 10 (100.0) | 10 (100.0) |
| | 24 hrs. | 10 (100.0) | 10 (100.0) | 10 (100.0) | 10 (100.0) | 10 (100.0) |
| | 48 hrs. | 10 (100.0) | 10 (100.0) | 10 (100.0) | 10 (100.0) | 10 (100.0) |
| Untreated | 1 min. | 0 (0.0) | 0 (0.0) | 0 (0.0) | 0 (0.0) | 0 (0.0) |
| | 5 min. | 0 (0.0) | 0 (0.0) | 0 (0.0) | 0 (0.0) | 0 (0.0) |
| | 10 min. | 0 (0.0) | 0 (0.0) | 0 (0.0) | 0 (0.0) | 0 (0.0) |
| | 1 hr. | 0 (0.0) | 0 (0.0) | 0 (0.0) | 0 (0.0) | 0 (0.0) |
| | 24 hrs. | 0 (0.0) | 0 (0.0) | 0 (0.0) | 0 (0.0) | 0 (0.0) |
| | 48 hrs. | 0 (0.0) | 0 (0.0) | 0 (0.0) | 0 (0.0) | 0 (0.0) |

EXAMPLE 7

Carpenter Ant, *Camponotus modoc*

| | |
|---|---|
| Life Stage: | Adult workers |
| Experimental Design: | Randomized Complete Block Design |
| Replication: | 4 |
| # Organisms per Replicate: | 10 |

Holding Conditions: Carpenter ants were field collected in Fresno County, Calif. The ants were held for about 24 hours prior to study initiation. The ants were then transferred into clear plastic cups (7.5 cm high×11 cm dia) and held at 70° F. The cup lids were removed during the test. Wood chips collected at the site were placed in the bottoms of the cups and the ants moved freely over the surface. Honey was provided as a food source.

Spray Application: A short burst of the unscented pesticidal composition, or the positive control pesticidal composition was directed at the test insects. No spray was applied to the untreated control. The spray canister was held 30 cm from the target. Complete spray coverage of the insects and wood surface was observed. The amount of product dispensed was determined by weighing the canister before and after each spray (Table 1).

Evaluation: The number of dead ants was assessed at 1, 5, and 10 minutes and at 1, 24, and 48 hours posttreatment. Death was defined as the inability of the organism to move when probed.

Results and Discussion: The carpenter ants initially became agitated after the spray application and then slowed down in movement. Mortality was relatively slow compared to the other insects tested. The test product, Eco PCO ACU (ADL-2-12-A) caused total kill within 24 hours after application, but Eco PCO AC (ADL-2-12-B) gave a high of 90% control at the final, 48 hour observation (Table 2). Complete survival was observed in the untreated group.

TABLE 1

Amount of product (grams) dispensed at each spray application-Carpenter ant.

| Treatment | Replicate 1 | 2 | 3 | 4 | Mean |
|---|---|---|---|---|---|
| Eco PCO ACU (ADL-2-12-A) | 0.8 | 0.8 | 1.0 | 0.7 | 0.8 |
| Eco PCO AC (ADL-2-12-B) | 1.1 | 0.5 | 0.9 | 0.5 | 0.8 |
| Untreated | 0.0 | 0.0 | 0.0 | 0.0 | 0.0 |

TABLE 2

Number of dead Carpenter ants (% mortality) n = 10 at
1, 5, and 10 minutes and 1, 24, and 48 hours posttreatment.

| Treatment | Posttreatment Time | Replicate 1 | 2 | 3 | 4 | Mean |
|---|---|---|---|---|---|---|
| Eco PCO ACU | 1 min. | 1 (10.0) | 2 (20.0) | 0 (0.0) | 0 (0.0) | 1 (7.5) |
| (ADL-2-12-A) | 5 min. | 3 (30.0) | 7 (70.0) | 5 (50.0) | 6 (60.0) | 5 (52.5) |
| | 10 min. | 3 (30.0) | 7 (70.0) | 6 (60.0) | 6 (60.0) | 6 (60.0) |
| | 1 hr. | 6 (60.0) | 8 (80.0) | 8 (80.0) | 10 (100.0) | 8 (80.0) |
| | 24 hrs. | 10 (100.0) | 10 (100.0) | 10 (100.0) | 10 (100.0) | 10 (100.0) |
| | 48 hrs. | 10 (100.0) | 10 (100.0) | 10 (100.0) | 10 (100.0) | 10 (100.0) |
| Eco PCO AC | 1 min. | 2 (20.0) | 1 (10.0) | 0 (0.0) | 1 (10.0) | 1 (10.0) |
| (ADL-2-12-B) | 5 min. | 4 (40.0) | 4 (40.0) | 0 (0.0) | 1 (10.0) | 2 (22.5) |
| | 10 min. | 4 (40.0) | 9 (90.0) | 5 (50.0) | 2 (20.0) | 5 (50.0) |
| | 1 hr. | 10 (100.0) | 10 (100.0) | 10 (100.0) | 6 (60.0) | 9 (90.0) |
| | 24 hrs. | 10 (100.0) | 10 (100.0) | 10 (100.0) | 6 (60.0) | 9 (90.0) |
| | 48 hrs. | 10 (100.0) | 10 (100.0) | 10 (100.0) | 6 (60.0) | 9 (90.0) |

TABLE 2-continued

Number of dead Carpenter ants (% mortality) n = 10 at
1, 5, and 10 minutes and 1, 24, and 48 hours posttreatment.

| Treatment | Posttreatment Time | Replicate 1 | 2 | 3 | 4 | Mean |
|---|---|---|---|---|---|---|
| Untreated | 1 min. | 0 (0.0) | 0 (0.0) | 0 (0.0) | 0 (0.0) | 0 (0.0) |
|  | 5 min. | 0 (0.0) | 0 (0.0) | 0 (0.0) | 0 (0.0) | 0 (0.0) |
|  | 10 min. | 0 (0.0) | 0 (0.0) | 0 (0.0) | 0 (0.0) | 0 (0.0) |
|  | 1 hr. | 0 (0.0) | 0 (0.0) | 0 (0.0) | 0 (0.0) | 0 (0.0) |
|  | 24 hrs. | 0 (0.0) | 0 (0.0) | 0 (0.0) | 0 (0.0) | 0 (0.0) |
|  | 48 hrs. | 0 (0.0) | 0 (0.0) | 0 (0.0) | 0 (0.0) | 0 (0.0) |

EXAMPLE 8

Cat flea, *Ctenocephalides felis*

| | |
|---|---|
| Life Stage: | Adult |
| Experimental Design: | Randomized Complete Block Design |
| Replication: | 4 |
| # Organisms per Replicate: | 10 |

Holding Conditions: Adult cat fleas were obtained from EL-Labs of Soquel, Calif. The fleas were held for about 3 hours prior to study initiation. Ten fleas were contained in each shipping vial along with a few wood shavings. A quick jar to the uncapped vials transferred the fleas into clear plastic cups (14 cm high×11 cm dia). The fleas were held at 70° F. during the test. The cup lids were secured until after the spray application. A circular disc of olefin fiber carpet (Bretlin Company, Calhoun, Ga.) was placed in the bottom of each cup and a clay border secured the edges of the carpet. The fleas moved freely over the carpet surface. No food or water was provided.

Spray Application: A short burst of the unscented pesticidal composition, or the positive control pesticidal composition was directed at the test insects. No spray was applied to the untreated control. The spray canister was held 30 cm from the target. Complete spray coverage of the insects and carpet surface was observed. The amount of product dispensed was determined by weighing the canister before and after each spray (Table 1).

Evaluation: The number of dead fleas was assessed at 1, 5, and 10 minutes and at 1, 24, and 48 hours posttreatment. Death was defined as the inability of the organism to move when probed.

Results and Discussion: All cat fleas were dead within 5 minutes after the spray application. Test product Eco PCO ACU caused 97.5% kill within 1 minute posttreatment and Eco PCO AC caused 87.5% mortality. No mortality occurred in the untreated group.

TABLE 1

Amount of product (grams) dispensed at each spray application - cat flea.

| Treatment | Replicate 1 | 2 | 3 | 4 | Mean |
|---|---|---|---|---|---|
| Eco PCO ACU (ADL-2-12-A) | 0.9 | 0.8 | 0.8 | 0.5 | 0.8 |
| Eco PCO AC (ADL-2-12-B) | 0.6 | 0.6 | 0.5 | 0.5 | 0.6 |
| Untreated | 0.0 | 0.0 | 0.0 | 0.0 | 0.0 |

TABLE 2

Number of dead cat fleas (% mortality) n = 10 at 1,
5, and 10 minutes and 1, 24, and 48 hours posttreatment.

| Treatment | Posttreatment Time | Replicate 1 | 2 | 3 | 4 | Mean |
|---|---|---|---|---|---|---|
| Eco PCO ACU | 1 min. | 9 (90.0) | 10 (100.0) | 10 (100.0) | 10 (100.0) | 10 (97.5) |
| (ADL-2-12-A) | 5 min. | 10 (100.0) | 10 (100.0) | 10 (100.0) | 10 (100.0) | 10 (100.0) |
|  | 10 min. | 10 (100.0) | 10 (100.0) | 10 (100.0) | 10 (100.0) | 10 (100.0) |
|  | 1 hr. | 10 (100.0) | 10 (100.0) | 10 (100.0) | 10 (100.0) | 10 (100.0) |
|  | 24 hrs. | 10 (100.0) | 10 (100.0) | 10 (100.0) | 10 (100.0) | 10 (100.0) |
|  | 48 hrs. | 10 (100.0) | 10 (100.0) | 10 (100.0) | 10 (100.0) | 10 (100.0) |
| Eco PCO AC | 1 min. | 10 (100.0) | 10 (100.0) | 8 (80.0) | 7 (70.0) | 9 (87.5) |
| (ADL-2-12-B) | 5 min. | 10 (100.0) | 10 (100.0) | 10 (100.0) | 10 (100.0) | 10 (100.0) |
|  | 10 min. | 10 (100.0) | 10 (100.0) | 10 (100.0) | 10 (100.0) | 10 (100.0) |
|  | 1 hr. | 10 (100.0) | 10 (100.0) | 10 (100.0) | 10 (100.0) | 10 (100.0) |
|  | 24 hrs. | 10 (100.0) | 10 (100.0) | 10 (100.0) | 10 (100.0) | 10 (100.0) |
|  | 48 hrs. | 10 (100.0) | 10 (100.0) | 10 (100.0) | 10 (100.0) | 10 (100.0) |
| Untreated | 1 min. | 0 (0.0) | 0 (0.0) | 0 (0.0) | 0 (0.0) | 0 (0.0) |
|  | 5 min. | 0 (0.0) | 0 (0.0) | 0 (0.0) | 0 (0.0) | 0 (0.0) |
|  | 10 min. | 0 (0.0) | 0 (0.0) | 0 (0.0) | 0 (0.0) | 0 (0.0) |

TABLE 2-continued

Number of dead cat fleas (% mortality) n = 10 at 1, 5, and 10 minutes and 1, 24, and 48 hours posttreatment.

| Treatment | Posttreatment Time | Replicate 1 | 2 | 3 | 4 | Mean |
|---|---|---|---|---|---|---|
| | 1 hr. | 0 (0.0) | 0 (0.0) | 0 (0.0) | 0 (0.0) | 0 (0.0) |
| | 24 hrs. | 0 (0.0) | 0 (0.0) | 0 (0.0) | 0 (0.0) | 0 (0.0) |
| | 48 hrs. | 0 (0.0) | 0 (0.0) | 0 (0.0) | 0 (0.0) | 0 (0.0) |

EXAMPLE 9

European Earwig, *Forficula auricularia*

| | |
|---|---|
| Life Stage: | Adult - 6 per replicate |
| | Nymph - 4 per replicate |
| Experimental Design: | Randomized Complete Block Design |
| Replication: | 3 |
| # Organisms per Replicate: | 10 |

Holding Conditions: Adults and nymphs of European earwigs were field collected in Fresno County, Calif. The earwigs were held for about 2 hours prior to study initiation. The earwigs were then transferred into clear plastic cups (7.5 cm high×11 cm dia) and held at 70° F. The cup lids were removed during the test. A circular disc of vinyl flooring was placed in the bottom of each cup, and the earwigs moved freely over the floor surface. No food or water was provided.

Spray Application: A short burst of the unscented pesticidal composition, or the positive control pesticidal composition was directed at the test insects. No spray was applied to the untreated control. The spray canister was held 30 cm from the target. Complete spray coverage of the insects and floor surface was observed. The amount of product dispensed was determined by weighing the canister before and after each spray (Table 1).

Evaluation: The number of earwigs was assessed at 1, 5, and 10 minutes and at 1, 24, and 48 hours posttreatment. Death was defined as the inability of the organism to move when probed.

Results and Discussion: The earwigs became agitated immediately upon being sprayed with the test products. At 1 minute posttreatment all earwigs were dead in the Eco PCO ACU (ADL-2-12-A) and Eco PCO AC (ADL-2-12-B) treatments. No recovery occurred.

TABLE 1

Amount of product (grams) dispensed at each spray application - European earwig.

| Treatment | Replicate 1 | 2 | 3 | Mean |
|---|---|---|---|---|
| Eco PCO ACU (ADL-2-12-A) | 1.5 | 1.5 | 1.6 | 1.5 |
| Eco PCO AC (ADL-2-12-B) | 0.7 | 1.2 | 1.2 | 1.0 |
| Untreated | 0.0 | 0.0 | 0.0 | 0.0 |

TABLE 2

Number of dead earwigs (% mortality) n = 10 at 1, 5, and 10 minutes and 1, 24, and 48 hours posttreatment.

| Treatment | Post-treatment Time | Replicate 1 | 2 | 3 | Mean |
|---|---|---|---|---|---|
| Eco PCO ACU (ADL-2-12-A) | 1 min. | 10 (100.0) | 10 (100.0) | 10 (100.0) | 10 (100.0) |
| | 5 min. | 10 (100.0) | 10 (100.0) | 10 (100.0) | 10 (100.0) |
| | 10 min. | 10 (100.0) | 10 (100.0) | 10 (100.0) | 10 (100.0) |
| | 1 hr. | 10 (100.0) | 10 (100.0) | 10 (100.0) | 10 (100.0) |
| | 24 hrs. | 10 (100.0) | 10 (100.0) | 10 (100.0) | 10 (100.0) |
| | 48 hrs. | 10 (100.0) | 10 (100.0) | 10 (100.0) | 10 (100.0) |
| Eco PCO AC (ADL-2-12-B) | 1 min. | 10 (100.0) | 10 (100.0) | 10 (100.0) | 10 (100.0) |
| | 5 min. | 10 (100.0) | 10 (100.0) | 10 (100.0) | 10 (100.0) |
| | 10 min. | 10 (100.0) | 10 (100.0) | 10 (100.0) | 10 (100.0) |
| | 1 hr. | 10 (100.0) | 10 (100.0) | 10 (100.0) | 10 (100.0) |
| | 24 hrs. | 10 (100.0) | 10 (100.0) | 10 (100.0) | 10 (100.0) |
| | 48 hrs. | 10 (100.0) | 10 (100.0) | 10 (100.0) | 10 (100.0) |
| Untreated | 1 min. | 0 (0.0) | 0 (0.0) | 0 (0.0) | 0 (0.0) |
| | 5 min. | 0 (0.0) | 0 (0.0) | 0 (0.0) | 0 (0.0) |
| | 10 min. | 0 (0.0) | 0 (0.0) | 0 (0.0) | 0 (0.0) |
| | 1 hr. | 0 (0.0) | 0 (0.0) | 0 (0.0) | 0 (0.0) |
| | 24 hrs. | 0 (0.0) | 0 (0.0) | 0 (0.0) | 0 (0.0) |
| | 48 hrs. | 0 (0.0) | 0 (0.0) | 0 (0.0) | 0 (0.0) |

EXAMPLE 10

Brown Dog Tick, *Rhipicephalus sanguineus*

| | |
|---|---|
| Life Stage: | Adult |
| Experimental Design: | Randomized Complete Block Design |
| Replication: | 4 |
| # Organisms per Replicate: | 10 |

Holding Conditions: Adult brown dog ticks were obtained from EL-Labs of Soquel, Calif. The ticks were held for about 3 hours prior to study initiation and were then transferred into clear plastic cups (7.5 cm high×11 cm dia) and held at 70° F. The cup lids were removed during the test. A circular disc of olefin fiber carpet (Bretlin Company, Calhoun, Ga.) was placed in the bottom of the cups, and the ticks moved freely over the carpet surface. A clay border around the carpet prevented the ticks from escaping along the edges. Ticks which moved onto the sides of the containers were gently brushed back onto the carpet surface. No food or water was provided.

Spray Application: A short burst of the unscented pesticidal composition, or the positive control pesticidal composition was directed at the test ticks. No spray was applied to the untreated control. The spray canister was held 30 cm from the target. Complete spray coverage of the ticks and carpet surface was observed. The amount of product dispensed was determined by weighing the canister before and after each spray (Table 1).

Evaluation: The number of dead ticks was assessed at 1, 5, and 10 minutes and at 1, 24, and 48 hours posttreatment. Death was defined as the inability of the organism to move when probed.

Results and Discussion: Both test products, Eco PCO ACU (ADL-2-12-A) and Eco PCO AC (ADL-2-12-B) caused complete kill of the adult ticks within 1 hour after the spray applications. Treatment with Eco PCO APU resulted in the best kill with 20.0%, 42.5%, and 80.0% mortality at 1, 5, and 10 minutes posttreatment whereas Eco PCO AC caused 5.0%, 37.5%, and 55% kill at the same time periods. No mortality occurred in the untreated group.

TABLE 1

Amount of product (grams) dispensed at each spray application - brown dog tick.

| Treatment | Replicate | | | | Mean |
| --- | --- | --- | --- | --- | --- |
| | 1 | 2 | 3 | 4 | |
| Eco PCO ACU (ADL-2-12-A) | 1.0 | 1.3 | 1.1 | 0.9 | 1.1 |
| Eco PCO AC (ADL-2-12-B) | 1.0 | 0.6 | 0.9 | 1.6 | 1.0 |
| Untreated | 0.0 | 0.0 | 0.0 | 0.0 | 0.0 |

EXAMPLE 11

Carpet Beetle, *Attagenus flavipes*

| Life Stage: | Mature larvae |
| --- | --- |
| Experimental Design: | Randomized Complete Block Design |
| Replication: | 4 |
| # Organisms per Replicate: | 10 |

Holding Conditions: Carpet beetle larvae were obtained from a colony maintained at the University fo California, Riverside. The larvae were held for one day prior to study initiation. Ten larvae were transferred onto circular discs of olefin fiber carper (Bretlin Company, Calhoun, Ga.). The carpet was held inside petri dishes (100 mm×15 mm). A small amount of feathers was placed on the carpet to serve as a food source. The larvae were held at 70° F. during the test.

Spray Application: A short burst of the unscented pesticidal composition, or the positive control pesticidal composition was directed at the test insects. No spray was applied to the untreated control. The spray canister was held 30 cm from the target. Complete spray coverage of the insects and carpet surface was observed. The amount of product dispensed was determined by weighing the canister before and after each spray (Table 1).

Evaluation: The number of dead larvae was assessed at 1, 5, and 10 minutes and at 1, 24, and 48 hours posttreatment. The larvae were examined under a dissecting microscope during the holdiong period. Death was defined as the inability of the organism to move when probed.

TABLE 2

Number of dead brown dog ticks (% mortality) n = 10 at 1, 5, and 10 minutes and 1, 24, and 48 hours posttreatment.

| Treatment | Posttreatment Time | Replicate | | | | Mean |
| --- | --- | --- | --- | --- | --- | --- |
| | | 1 | 2 | 3 | 4 | |
| Eco PCO ACU (ADL-2-12-A) | 1 min. | 2 (20.0) | 3 (30.0) | 1 (10.0) | 2 (20.0) | 2 (20.0) |
| | 5 min. | 4 (40.0) | 5 (50.0) | 3 (30.0) | 5 (50.0) | 4 (42.5) |
| | 10 min. | 9 (90.0) | 9 (90.0) | 6 (60.0) | 8 (80.0) | 8 (80.0) |
| | 1 hr. | 10 (100.0) | 10 (100.0) | 10 (100.0) | 10 (100.0) | 10 (100.0) |
| | 24 hrs. | 10 (100.0) | 10 (100.0) | 10 (100.0) | 10 (100.0) | 10 (100.0) |
| | 48 hrs. | 10 (100.0) | 10 (100.0) | 10 (100.0) | 10 (100.0) | 10 (100.0) |
| Eco PCO AC (ADL-2-12-B) | 1 min. | 2 (20.0) | 0 (0.0) | 0 (0.0) | 0 (0.0) | 1 (5.0) |
| | 5 min. | 7 (70.0) | 2 (20.0) | 4 (40.0) | 2 (20.0) | 4 (37.5) |
| | 10 min. | 8 (80.0) | 4 (40.0) | 5 (50.0) | 5 (50.0) | 6 (55.0) |
| | 1 hr. | 10 (100.0) | 10 (100.0) | 10 (100.0) | 10 (100.0) | 10 (100.0) |
| | 24 hrs. | 10 (100.0) | 10 (100.0) | 10 (100.0) | 10 (100.0) | 10 (100.0) |
| | 48 hrs. | 10 (100.0) | 10 (100.0) | 10 (100.0) | 10 (100.0) | 10 (100.0) |
| Untreated | 1 min. | 0 (0.0) | 0 (0.0) | 0 (0.0) | 0 (0.0) | 0 (0.0) |
| | 5 min. | 0 (0.0) | 0 (0.0) | 0 (0.0) | 0 (0.0) | 0 (0.0) |
| | 10 min. | 0 (0.0) | 0 (0.0) | 0 (0.0) | 0 (0.0) | 0 (0.0) |
| | 1 hr. | 0 (0.0) | 0 (0.0) | 0 (0.0) | 0 (0.0) | 0 (0.0) |
| | 24 hrs. | 0 (0.0) | 0 (0.0) | 0 (0.0) | 0 (0.0) | 0 (0.0) |
| | 48 hrs. | 0 (0.0) | 0 (0.0) | 0 (0.0) | 0 (0.0) | 0 (0.0) |

Results and Discussion: All carpet beetle larvae were dead within 1 minute after the spray application. Test product Eco PCO ACU and Eco PCO AC both caused total mortality. No mortality occurred in the untreated group.

TABLE 1

Amount of product (grams) dispensed at each spray application - Carpet beetle larvae.

| Treatment | Replicate | | | | Mean |
|---|---|---|---|---|---|
| | 1 | 2 | 3 | 4 | |
| Eco PCO ACU (ADL-2-12-A) | 0.5 | 0.5 | 0.7 | 0.5 | 0.6 |
| Eco PCO AC (ADL-2-12-B) | 0.7 | 0.5 | 0.5 | 0.4 | 0.5 |
| Untreated | 0.0 | 0.0 | 0.0 | 0.0 | 0.0 | of the unscented pesticidal composition, or the positive control pesticidal composition was then directed at the test insects by spraying through the portal. No spray was applied to the untreated control. Complete spray coverage of the insects and the interior surface of the cylinder was observed. The amount of product dispensed was determined by weighing the canister before and after each spray (Table 1).

Evaluation: The number of dead flies was assessed at 1, 5, and 10 minutes and at 1, 24, and 48 hours posttreatment. Death was defined as the inability of the organism to move when probed.

Results and Discussion: House flies were knocked down immediately upon being sprayed with the test products. At 1 minute posttreatment all (100.0%) of the flies were dead in the treatment of Eco PCO ACU (ADL-2-12-A), compared to 97.5% in the treatment with Eco PCO AC (ADL-2-12-B) (Table 2). All sprayed flies were dead within 5 minutes in the

TABLE 2

Number of dead carpet beetle larvae (% mortality) n = 10 at 1, 5, and 10 minutes and 1, 24, and 48 hours posttreatment

| Treatment | Posttreatment Time | Replicate | | | | Mean |
|---|---|---|---|---|---|---|
| | | 1 | 2 | 3 | 4 | |
| Eco PCO ACU (ADL-2-12-A) | 1 min. | 10 (100.0) | 10 (100.0) | 10 (100.0) | 10 (100.0) | 10 (100.0) |
| | 5 min. | 10 (100.0) | 10 (100.0) | 10 (100.0) | 10 (100.0) | 10 (100.0) |
| | 10 min. | 10 (100.0) | 10 (100.0) | 10 (100.0) | 10 (100.0) | 10 (100.0) |
| | 1 hr. | 10 (100.0) | 10 (100.0) | 10 (100.0) | 10 (100.0) | 10 (100.0) |
| | 24 hrs. | 10 (100.0) | 10 (100.0) | 10 (100.0) | 10 (100.0) | 10 (100.0) |
| | 48 hrs. | 10 (100.0) | 10 (100.0) | 10 (100.0) | 10 (100.0) | 10 (100.0) |
| Eco PCO AC (ADL-2-12-B) | 1 min. | 10 (100.0) | 10 (100.0) | 10 (100.0) | 10 (100.0) | 10 (100.0) |
| | 5 min. | 10 (100.0) | 10 (100.0) | 10 (100.0) | 10 (100.0) | 10 (100.0) |
| | 10 min. | 10 (100.0) | 10 (100.0) | 10 (100.0) | 10 (100.0) | 10 (100.0) |
| | 1 hr. | 10 (100.0) | 10 (100.0) | 10 (100.0) | 10 (100.0) | 10 (100.0) |
| | 24 hrs. | 10 (100.0) | 10 (100.0) | 10 (100.0) | 10 (100.0) | 10 (100.0) |
| | 48 hrs. | 10 (100.0) | 10 (100.0) | 10 (100.0) | 10 (100.0) | 10 (100.0) |
| Untreated | 1 min. | 0 (0.0) | 0 (0.0) | 0 (0.0) | 0 (0.0) | 0 (0.0) |
| | 5 min. | 0 (0.0) | 0 (0.0) | 0 (0.0) | 0 (0.0) | 0 (0.0) |
| | 10 min. | 0 (0.0) | 0 (0.0) | 0 (0.0) | 0 (0.0) | 0 (0.0) |
| | 1 hr. | 0 (0.0) | 0 (0.0) | 0 (0.0) | 0 (0.0) | 0 (0.0) |
| | 24 hrs. | 0 (0.0) | 0 (0.0) | 0 (0.0) | 0 (0.0) | 0 (0.0) |
| | 48 hrs. | 0 (0.0) | 0 (0.0) | 0 (0.0) | 0 (0.0) | 0 (0.0) |

EXAMPLE 12

House Fly, *Musca domestica*

| Life Stage: | Adult |
|---|---|
| Experimental Design: | Randomized Complete Block Design |
| Replication: | 4 |
| # Organisms per Replicate: | 10 |

Holding Conditions:

House flies were obtained as puparium from Rincon-Vitova Insectaries, Inc. of Ventura, Calif. After emergence as adults they were transferred into plastic cylinders (22.0 cm high×9.0 cm diameter) with a screen at one end and a spray portal at the opposite end, and held at 70° F. The cup lids were removed during the test. Flies moved freely inside the cage. No food or water was provided.

Spray Application: A "soda straw" (provided with the canisters) was attached to the canister nozzle. A short burst ECO PCO AC (ADL-2-12-B) treatment. Complete survival was observed in the untreated group.

TABLE 1

Amount of product (grams) dispensed at each spray application - House fly.

| Treatment | Replicate | | | | Mean |
|---|---|---|---|---|---|
| | 1 | 2 | 3 | 4 | |
| Eco PCO ACU (ADL-2-12-A) | 0.6 | 0.5 | 0.7 | 0.5 | 0.6 |
| Eco PCO AC (ADL-2-12-B) | 1.0 | 0.6 | 0.7 | 0.5 | 0.7 |
| Untreated | 0.0 | 0.0 | 0.0 | 0.0 | 0.0 |

TABLE 2

Number of dead house flies (% mortality) n = 10 at 1,
5, and 10 minutes and 1, 24, and 48 hours posttreatment.

| Treatment | Posttreatment Time | Replicate 1 | 2 | 3 | 4 | Mean |
|---|---|---|---|---|---|---|
| Eco PCO ACU (ADL-2-12-A) | 1 min. | 10 (100.0) | 10 (100.0) | 10 (100.0) | 10 (100.0) | 10 (100.0) |
|  | 5 min. | 10 (100.0) | 10 (100.0) | 10 (100.0) | 10 (100.0) | 10 (100.0) |
|  | 10 min. | 10 (100.0) | 10 (100.0) | 10 (100.0) | 10 (100.0) | 10 (100.0) |
|  | 1 hr. | 10 (100.0) | 10 (100.0) | 10 (100.0) | 10 (100.0) | 10 (100.0) |
|  | 24 hrs. | 10 (100.0) | 10 (100.0) | 10 (100.0) | 10 (100.0) | 10 (100.0) |
|  | 48 hrs. | 10 (100.0) | 10 (100.0) | 10 (100.0) | 10 (100.0) | 10 (100.0) |
| Eco PCO AC (ADL-2-12-B) | 1 min. | 10 (100.0) | 10 (100.0) | 10 (100.0) | 9 (90.0) | 10 (97.5) |
|  | 5 min. | 10 (100.0) | 10 (100.0) | 10 (100.0) | 10 (100.0) | 10 (100.0) |
|  | 10 min. | 10 (100.0) | 10 (100.0) | 10 (100.0) | 10 (100.0) | 10 (100.0) |
|  | 1 hr. | 10 (100.0) | 10 (100.0) | 10 (100.0) | 10 (100.0) | 10 (100.0) |
|  | 24 hrs. | 10 (100.0) | 10 (100.0) | 10 (100.0) | 10 (100.0) | 10 (100.0) |
|  | 48 hrs. | 10 (100.0) | 10 (100.0) | 10 (100.0) | 10 (100.0) | 10 (100.0) |
| Untreated | 1 min. | 0 (0.0) | 0 (0.0) | 0 (0.0) | 0 (0.0) | 0 (0.0) |
|  | 5 min. | 0 (0.0) | 0 (0.0) | 0 (0.0) | 0 (0.0) | 0 (0.0) |
|  | 10 min. | 0 (0.0) | 0 (0.0) | 0 (0.0) | 0 (0.0) | 0 (0.0) |
|  | 1 hr. | 0 (0.0) | 0 (0.0) | 0 (0.0) | 0 (0.0) | 0 (0.0) |
|  | 24 hrs. | 0 (0.0) | 0 (0.0) | 0 (0.0) | 0 (0.0) | 0 (0.0) |
|  | 48 hrs. | 0 (0.0) | 0 (0.0) | 0 (0.0) | 0 (0.0) | 0 (0.0) |

EXAMPLE 13

Field Cricket, *Acheta assimilis*

| | |
|---|---|
| Life Stage: | Adult |
| Experimental Design: | Randomized Complete Block Design |
| Replication: | 4 |
| # Organisms per Replicate: | 10 |

Holding Conditions: Field crickets were obtained from a local insectary. The crickets were held for about 3 hours prior to study initiation. The crickets were then transferred into clear plastic cups (7.5 cm high×11 cm dia) and held at 70° F. The cup lids were removed during the test. A circular disc of vinyl flooring was placed in the bottom of each cup, and the crickets moved freely over the floor surface. No food or water was provided.

Spray Application: A short burst of the unscented pesticidal composition, or the positive control pesticidal composition was directed at the test insects. No spray was applied to the untreated control. The spray canister was held 30 cm from the target. Complete spray coverage of the insects and floor surface was observed. The amount of product dispensed was determined by weighing the canister before and after each spray (Table 1).

Evaluation: The number of dead crickets was assessed at 1, 5, and 10 minutes and at 1, 24, and 48 hours posttreatment. Death was defined as the inability of the organism to move when probed.

Results and Discussion: All crickets were dead within 1 minute after the spray application of EcoPCO ACU (ADL-2-12-A) (Table 2). An average of 87.5% death occurred in the positive control pesticidal composition within the same time frame, and total death occurred within 5 minutes. No death occurred in the untreated group during the holding period.

TABLE 1

Amount of product (grams) dispensed at each spray application - field cricket.

| Treatment | Replicate 1 | 2 | 3 | 4 | Mean |
|---|---|---|---|---|---|
| Eco PCO ACU (ADL-2-12-A) | 0.5 | 0.5 | 0.8 | 0.8 | 0.7 |
| Eco PCO AC (ADL-2-12-B) | 0.4 | 0.4 | 0.5 | 0.5 | 0.5 |
| Untreated | 0.0 | 0.0 | 0.0 | 0.0 | 0.0 |

TABLE 2

Number of dead crickets (% mortality) n = 10 at 1,
5, and 10 minutes and 1, 24, and 48 hours posttreatment.

| Treatment | Posttreatment Time | Replicate 1 | 2 | 3 | 4 | Mean |
|---|---|---|---|---|---|---|
| Eco PCO ACU (ADL-2-12-A) | 1 min. | 10 (100.0) | 10 (100.0) | 10 (100.0) | 10 (100.0) | 10 (100.0) |
|  | 5 min. | 10 (100.0) | 10 (100.0) | 10 (100.0) | 10 (100.0) | 10 (100.0) |
|  | 10 min. | 10 (100.0) | 10 (100.0) | 10 (100.0) | 10 (100.0) | 10 (100.0) |
|  | 1 hr. | 10 (100.0) | 10 (100.0) | 10 (100.0) | 10 (100.0) | 10 (100.0) |
|  | 24 hrs. | 10 (100.0) | 10 (100.0) | 10 (100.0) | 10 (100.0) | 10 (100.0) |
|  | 48 hrs. | 10 (100.0) | 10 (100.0) | 10 (100.0) | 10 (100.0) | 10 (100.0) |

TABLE 2-continued

Number of dead crickets (% mortality) n = 10 at 1,
5, and 10 minutes and 1, 24, and 48 hours posttreatment.

| Treatment | Posttreatment Time | Replicate 1 | 2 | 3 | 4 | Mean |
|---|---|---|---|---|---|---|
| Eco PCO AC (ADL-2-12-B) | 1 min. | 7 (70.0) | 10 (100.0) | 8 (80.0) | 10 (100.0) | 9 (87.5) |
|  | 5 min. | 10 (100.0) | 10 (100.0) | 10 (100.0) | 10 (100.0) | 10 (100.0) |
|  | 10 min. | 10 (100.0) | 10 (100.0) | 10 (100.0) | 10 (100.0) | 10 (100.0) |
|  | 1 hr. | 10 (100.0) | 10 (100.0) | 10 (100.0) | 10 (100.0) | 10 (100.0) |
|  | 24 hrs. | 10 (100.0) | 10 (100.0) | 10 (100.0) | 10 (100.0) | 10 (100.0) |
|  | 48 hrs. | 10 (100.0) | 10 (100.0) | 10 (100.0) | 10 (100.0) | 10 (100.0) |
| Untreated | 1 min. | 0 (0.0) | 0 (0.0) | 0 (0.0) | 0 (0.0) | 0 (0.0) |
|  | 5 min. | 0 (0.0) | 0 (0.0) | 0 (0.0) | 0 (0.0) | 0 (0.0) |
|  | 10 min. | 0 (0.0) | 0 (0.0) | 0 (0.0) | 0 (0.0) | 0 (0.0) |
|  | 1 hr. | 0 (0.0) | 0 (0.0) | 0 (0.0) | 0 (0.0) | 0 (0.0) |
|  | 24 hrs. | 0 (0.0) | 0 (0.0) | 0 (0.0) | 0 (0.0) | 0 (0.0) |
|  | 48 hrs. | 0 (0.0) | 0 (0.0) | 0 (0.0) | 0 (0.0) | 0 (0.0) |

EXAMPLE 14

American Cockroach, *Periplaneta americana*

| | |
|---|---|
| Life Stage: | Adult |
| Experimental Design: | Randomized Complete Block Design |
| Replication: | 4 |
| # Organisms per Replicate: | 5 |

Holding Conditions: American cockroaches were obtained from a colony maintained at S. C. Johnson & Sons, Racine, Wis. The cockroaches were held for about 2 days prior to study initiation. The cockroaches were then transferred into clear plastic cups (7.5 cm high×11 cm diameter) and held at 70° F. The cup lids were removed during the test. A circular disc of vinyl flooring was placed in the bottom of each cup and Fluon (polytetrafluoroethylene) was painted on the inside of the cups. Fluon is a dry lubricant and prevented the cockroaches from crawling up the sides of the cup. The cockroaches moved freely over the floor surface. No food or water was provided.

Spray Application: A short burst of the unscented pesticidal composition, or the positive control pesticidal composition was directed at the test insects. No spray was applied to the untreated control. The spray canister was held 30 cm from the target. Complete spray coverage of the insects and floor surface was observed. The amount of product dispensed was determined by weighing the canister before and after each spray (Table 1).

Evaluation: The number of dead cockroaches was assessed at 1, 5, and 10 minutes and at 1, 24, and 48 hours posttreatment. Death was defined as the inability of the organism to move when probed.

Results and Discussion: The cockroaches became agitated immediately upon being sprayed with the test products. At 1 minute posttreatment 30.0% of the cockroaches were dead in the treatment of Eco PCO ACU (ADL-2-12-A), compared to 10.0% in the treatment with Eco PCO AC (ADL-2-12-B) (Table 2). All sprayed cockroaches were dead within 5 minutes in the Eco PCO ACU (ADL-2-12-A) treatment, whereas it took 10 minutes for total kill in the Eco PCO AC (ADL-2-12-B) treatment. No mortality occurred in the untreated group.

TABLE 1

Amount of product (grams) dispensed at each
spray application - American cockroach.

| Treatment | Replicate 1 | 2 | 3 | 4 | Mean |
|---|---|---|---|---|---|
| Eco PCO ACU (ADL-2-12-A) | 1.3 | 1.1 | 0.7 | 1.1 | 1.0 |
| Eco PCO AC (ADL-2-12-B) | 0.8 | 0.8 | 0.6 | 0.8 | 0.8 |
| Untreated | 0.0 | 0.0 | 0.0 | 0.0 | 0.0 |

TABLE 2

Number of dead American cockroaches (% mortality) n = 5 at
1, 5, and 10 minutes and 1, 24, and 48 hours posttreatment.

| Treatment | Posttreatment Time | Replicate 1 | 2 | 3 | 4 | Mean |
|---|---|---|---|---|---|---|
| Eco PCO ACU (ADL-2-12-A) | 1 min. | 1 (20.0) | 1 (20.0) | 1 (20.0) | 3 (60.0) | 1 (30.0) |
|  | 5 min. | 5 (100.0) | 5 (100.0) | 5 (100.0) | 5 (100.0) | 5 (100.0) |
|  | 10 min. | 5 (100.0) | 5 (100.0) | 5 (100.0) | 5 (100.0) | 5 (100.0) |
|  | 1 hr. | 5 (100.0) | 5 (100.0) | 5 (100.0) | 5 (100.0) | 5 (100.0) |
|  | 24 hrs. | 5 (100.0) | 5 (100.0) | 5 (100.0) | 5 (100.0) | 5 (100.0) |
|  | 48 hrs. | 5 (100.0) | 5 (100.0) | 5 (100.0) | 5 (100.0) | 5 (100.0) |

TABLE 2-continued

Number of dead American cockroaches (% mortality) n = 5 at
1, 5, and 10 minutes and 1, 24, and 48 hours posttreatment.

| Treatment | Posttreatment Time | Replicate 1 | 2 | 3 | 4 | Mean |
|---|---|---|---|---|---|---|
| Eco PCO AC | 1 min. | 0 (0.0) | 1 (20.0) | 0 (0.0) | 1 (20.0) | 1 (10.0) |
| (ADL-2-12-B) | 5 min. | 5 (100.0) | 5 (100.0) | 4 (80.0) | 5 (100.0) | 4 (95.0) |
|  | 10 min. | 5 (100.0) | 5 (100.0) | 5 (100.0) | 5 (100.0) | 5 (100.0) |
|  | 1 hr. | 5 (100.0) | 5 (100.0) | 5 (100.0) | 5 (100.0) | 5 (100.0) |
|  | 24 hrs. | 5 (100.0) | 5 (100.0) | 5 (100.0) | 5 (100.0) | 5 (100.0) |
|  | 48 hrs. | 5 (100.0) | 5 (100.0) | 5 (100.0) | 5 (100.0) | 5 (100.0) |
| Untreated | 1 min. | 0 (0.0) | 0 (0.0) | 0 (0.0) | 0 (0.0) | 0 (0.0) |
|  | 5 min. | 0 (0.0) | 0 (0.0) | 0 (0.0) | 0 (0.0) | 0 (0.0) |
|  | 10 min. | 0 (0.0) | 0 (0.0) | 0 (0.0) | 0 (0.0) | 0 (0.0) |
|  | 1 hr. | 0 (0.0) | 0 (0.0) | 0 (0.0) | 0 (0.0) | 0 (0.0) |
|  | 24 hrs. | 0 (0.0) | 0 (0.0) | 0 (0.0) | 0 (0.0) | 0 (0.0) |
|  | 48 hrs. | 0 (0.0) | 0 (0.0) | 0 (0.0) | 0 (0.0) | 0 (0.0) |

EXAMPLE 15

German Cockroach, *Blatella germanica*

| Life Stage: | Adult |
|---|---|
| Experimental Design: | Randomized Complete Block Design |
| Replication: | 4 |
| # Organisms per Replicate: | 10 |

Holding Conditions: German cockroaches were field collected from infested apartments in Fresno, California. The cockroaches were held for about 4 days prior to study initiation. The cockroaches were then transferred into clear plastic cups (7.5 cm high×11 cm diameter) and held at 70° F. The cup lids were removed during the test. A circular disc of vinyl flooring was placed in the bottom of each cup and Fluon (polytetrafluoroethylene) was painted on the inside of the cups. Fluon is a dry lubricant and prevented the cockroaches from crawling up the sides of the cup. The cockroaches moved freely over the floor surface. No food or water was provided.

Spray Application: A short burst of the unscented pesticidal composition, or the positive control pesticidal composition was directed at the test insects. No spray was applied to the untreated control. The spray canister was held 30 cm from the target. Complete spray coverage of the insects and floor surface was observed. The amount of product dispensed was determined by weighing the canister before and after each spray (Table 1).

Evaluation: The number of dead cockroaches was assessed at 1, 5, and 10 minutes and at 1, 24, and 48 hours posttreatment. Death was defined as the inability of the organism to move when probed.

Results and Discussion: The cockroaches became agitated immediately upon being sprayed with the test products. At 1 minute posttreatment total (100%) of the cockroaches were dead in the treatment of Eco PCO ACU (ADL-2-12-A), compared to 95% in the treatment with Eco PCO AC (ADL-2-12-B) (Table 2). All sprayed cockroaches were dead in both treatments within 5 minutes. Only slight mortality occurred in the untreated group.

TABLE 1

Amount of product (grams) dispensed at each spray application - German cockroach.

| Treatment | Replicate 1 | 2 | 3 | 4 | Mean |
|---|---|---|---|---|---|
| Eco PCO ACU (ADL-2-12-A) | 1.0 | 0.5 | 0.6 | 0.8 | 0.7 |
| Eco PCO AC (ADL-2-12-B) | 0.8 | 0.9 | 0.5 | 0.5 | 0.7 |
| Untreated | 0.0 | 0.0 | 0.0 | 0.0 | 0.0 |

TABLE 2

Number of dead German cockroaches (% mortality) n = 10 at
1, 5, and 10 minutes and 1, 24, and 48 hours posttreatment.

| Treatment | Posttreatment Time | Replicate 1 | 2 | 3 | 4 | Mean |
|---|---|---|---|---|---|---|
| Eco PCO ACU | 1 min. | 9 (90.0) | 10 (100.0) | 9 (90.0) | 10 (100.0) | 9 (95.0) |
| (ADL-2-12-A) | 5 min. | 10 (100.0) | 10 (100.0) | 10 (100.0) | 10 (100.0) | 10 (100.0) |
|  | 10 min. | 10 (100.0) | 10 (100.0) | 10 (100.0) | 10 (100.0) | 10 (100.0) |
|  | 1 hr. | 10 (100.0) | 10 (100.0) | 10 (100.0) | 10 (100.0) | 10 (100.0) |
|  | 24 hrs. | 10 (100.0) | 10 (100.0) | 10 (100.0) | 10 (100.0) | 10 (100.0) |
|  | 48 hrs. | 10 (100.0) | 10 (100.0) | 10 (100.0) | 10 (100.0) | 10 (100.0) |

TABLE 2-continued

Number of dead German cockroaches (% mortality) n = 10 at
1, 5, and 10 minutes and 1, 24, and 48 hours posttreatment.

| Treatment | Posttreatment Time | Replicate 1 | 2 | 3 | 4 | Mean |
|---|---|---|---|---|---|---|
| Eco PCO AC | 1 min. | 10 (100.0) | 10 (100.0) | 10 (100.0) | 10 (100.0) | 10 (100.0) |
|  | 5 min. | 10 (100.0) | 10 (100.0) | 10 (100.0) | 10 (100.0) | 10 (100.0) |
|  | 10 min. | 10 (100.0) | 10 (100.0) | 10 (100.0) | 10 (100.0) | 10 (100.0) |
|  | 1 hr. | 10 (100.0) | 10 (100.0) | 10 (100.0) | 10 (100.0) | 10 (100.0) |
|  | 24 hrs. | 10 (100.0) | 10 (100.0) | 10 (100.0) | 10 (100.0) | 10 (100.0) |
|  | 48 hrs. | 10 (100.0) | 10 (100.0) | 10 (100.0) | 10 (100.0) | 10 (100.0) |
| Untreated | 1 min. | 0 (0.0) | 0 (0.0) | 0 (0.0) | 0 (0.0) | 0 (0.0) |
|  | 5 min. | 0 (0.0) | 0 (0.0) | 0 (0.0) | 0 (0.0) | 0 (0.0) |
|  | 10 min. | 0 (0.0) | 0 (0.0) | 0 (0.0) | 0 (0.0) | 0 (0.0) |
|  | 1 hr. | 1 (10.0) | 0 (0.0) | 0 (0.0) | 0 (0.0) | 1 (2.5) |
|  | 24 hrs. | 1 (10.0) | 0 (0.0) | 0 (0.0) | 0 (0.0) | 1 (2.5) |
|  | 48 hrs. | 1 (10.0) | 0 (0.0) | 1 (10.0) | 0 (0.0) | 2 (5.0) |

EXAMPLE 16

Paper Wasp, *Polistes prob. fuscatus*

| | |
|---|---|
| Life Stage: | Adult |
| Experimental Design: | Randomized Complete Block Design |
| Replication: | 4 |
| # Organisms per Replicate: | 5 |

Holding Conditions: Paper wasps were field collected in Fresno County, California and held for 1 day prior to test initiation. The wasps were transferred into plastic cylinders (22.0 cm high×9.0 cm diameter) with a screen at one end and a spray portal at the opposite end, and held at 70° F. The wasps moved freely inside the cage. Honey was provided as food.

Spray Application: A "soda straw" (provided with the canisters) was attached to the canister nozzles. A short burst of the unscented pesticidal composition, or the positive control pesticidal composition was then directed at the test insects by spraying through the portal. No spray was applied to the untreated control. Complete spray coverage of the insects and the interior surface of the cylinder was observed. The amount of product dispensed was determined by weighing the canister before and after each spray (Table 1).

Evaluation: The number of dead wasps was assessed at 1, 5, and 10 minutes and at 1, 24, and 48 hours posttreatment. Death was defined as the inability of the organism to move when probed.

Results and Discussion: The paper wasps were knocked down immediately upon being sprayed with the test products. At 10 minutes posttreatment all (100.0%) of the wasps were dead in the treatment of Eco PCO ACU (ADL-2-12-A), and at 5 minutes all (100%) of the wasps were dead in the Eco PCO AC (ADL-2-12-B) treatment (Table 2).

TABLE 1

Amount of product (grams) dispensed at each spray application - Paper wasp.

| Treatment | Replicate 1 | 2 | 3 | 4 | Mean |
|---|---|---|---|---|---|
| Eco PCO ACU (ADL-2-12-A) | 1.0 | 0.6 | 0.8 | 1.2 | 0.9 |
| Eco PCO AC (ADL-2-12-B) | 1.0 | 1.0 | 1.0 | 1.2 | 1.1 |
| Untreated | 0.0 | 0.0 | 0.0 | 0.0 | 0.0 |

TABLE 2

Number of dead paper wasps (% mortality) n = 5 at 1,
5, and 10 minutes and 1, 24, and 48 hours posttreatment.

| Treatment | Posttreatment Time | Replicate 1 | 2 | 3 | 4 | Mean |
|---|---|---|---|---|---|---|
| Eco PCO ACU (ADL-2-12-A) | 1 min. | 4 (80.0) | 1 (20.0) | 2 (40.0) | 1 (20.0) | 2 (40.0) |
|  | 5 min. | 5 (100.0) | 3 (60.0) | 4 (80.0) | 3 (60.0) | 4 (75.0) |
|  | 10 min. | 5 (100.0) | 5 (100.0) | 5 (100.0) | 5 (100.0) | 5 (100.0) |
|  | 1 hr. | 5 (100.0) | 5 (100.0) | 5 (100.0) | 5 (100.0) | 5 (100.0) |
|  | 24 hrs. | 5 (100.0) | 5 (100.0) | 5 (100.0) | 5 (100.0) | 5 (100.0) |
|  | 48 hrs. | 5 (100.0) | 5 (100.0) | 5 (100.0) | 5 (100.0) | 5 (100.0) |
| Eco PCO AC (ADL-2-12-B) | 1 min. | 2 (40.0) | 2 (40.0) | 2 (40.0) | 4 (80.0) | 3 (50.0) |
|  | 5 min. | 5 (100.0) | 5 (100.0) | 5 (100.0) | 5 (100.0) | 5 (100.0) |
|  | 10 min. | 5 (100.0) | 5 (100.0) | 5 (100.0) | 5 (100.0) | 5 (100.0) |
|  | 1 hr. | 5 (100.0) | 5 (100.0) | 5 (100.0) | 5 (100.0) | 5 (100.0) |

TABLE 2-continued

Number of dead paper wasps (% mortality) n = 5 at 1, 5, and 10 minutes and 1, 24, and 48 hours posttreatment.

| Treatment | Posttreatment Time | Replicate 1 | 2 | 3 | 4 | Mean |
|---|---|---|---|---|---|---|
| | 24 hrs. | 5 (100.0) | 5 (100.0) | 5 (100.0) | 5 (100.0) | 5 (100.0) |
| | 48 hrs. | 5 (100.0) | 5 (100.0) | 5 (100.0) | 5 (100.0) | 5 (100.0) |
| Untreated | 1 min. | 0 (0.0) | 0 (0.0) | 0 (0.0) | 0 (0.0) | 0 (0.0) |
| | 5 min. | 0 (0.0) | 0 (0.0) | 0 (0.0) | 0 (0.0) | 0 (0.0) |
| | 10 min. | 0 (0.0) | 0 (0.0) | 0 (0.0) | 0 (0.0) | 0 (0.0) |
| | 1 hr. | 0 (0.0) | 0 (0.0) | 0 (0.0) | 0 (0.0) | 0 (0.0) |
| | 24 hrs. | 0 (0.0) | 0 (0.0) | 0 (0.0) | 0 (0.0) | 0 (0.0) |
| | 48 hrs. | 0 (0.0) | 0 (0.0) | 0 (0.0) | 1 (20.0) | 1 (5.0) |

EXAMPLE 17

Western Subterranean Termite, *Reticulitermes hesperus*

| | |
|---|---|
| Life Stage: | Adult workers |
| Experimental Design: | Randomized Complete Block Design |
| Replication: | 4 |
| # Organisms per Replicate: | 10 |

Holding Conditions: Termites were field collected in Fresno County, Calif. They were held for about 1 hour prior to study initiation. The termites were then transferred into clear plastic cups (7.5 cm high×11 cm dia) and held at 70° F. The cup lids were removed during the test. A circular disc of vinyl flooring was placed in the bottom of each cup, and the termites moved freely over the floor surface. No food or water was provided.

Spray Application: A short burst of the unscented pesticidal composition, or the positive control pesticidal composition was directed at the test organisms. No spray was applied to the untreated control. The spray canister was held 30 cm from the target. Complete spray coverage of the termites and floor surface was observed. The amount of product dispensed was determined by weighing the canister before and after each spray (Table 1).

Evaluation: The number of dead termites was assessed at 1, 5, and 10 minutes and at 1, 24, and 48 hours posttreatment. Death was defined as the inability of the organism to move when probed.

Results and Discussion: One minute after treatment all (100%) of the termites sprayed with Eco PCO ACU (ADL-2-12-A) and Eco PCO AC (ADL-2-12-B) were dead. No mortality occurred in the untreated group during the first 6 hours of the test. It then increased to 100% death by 48 hours. This was likely due to the low humidity in the test cages and/or lack of food. This late mortality, however, likely had no affect on the results of the experiment.

TABLE 1

Amount of product (grams) dispensed at each spray application - Termite.

| Treatment | Replicate 1 | 2 | 3 | 4 | Mean |
|---|---|---|---|---|---|
| Eco PCO ACU (ADL-2-12-A) | 1.0 | 1.1 | 1.3 | 0.9 | 1.1 |
| Eco PCO AC (ADL-2-12-B) | 1.1 | 0.7 | 0.6 | 0.8 | 0.8 |
| Untreated | 0.0 | 0.0 | 0.0 | 0.0 | 0.0 |

TABLE 2

Number of dead termites (% mortality) n = 10 at 1, 5, and 10 minutes and 1, 24, and 48 hours posttreatment.

| Treatment | Posttreatment Time | Replicate 1 | 2 | 3 | 4 | Mean |
|---|---|---|---|---|---|---|
| Eco PCO ACU | 1 min. | 10 (100.0) | 10 (100.0) | 10 (100.0) | 10 (100.0) | 10 (100.0) |
| (ADL-2-12-A) | 5 min. | 10 (100.0) | 10 (100.0) | 10 (100.0) | 10 (100.0) | 10 (100.0) |
| | 10 min. | 10 (100.0) | 10 (100.0) | 10 (100.0) | 10 (100.0) | 10 (100.0) |
| | 1 hr. | 10 (100.0) | 10 (100.0) | 10 (100.0) | 10 (100.0) | 10 (100.0) |
| | 24 hrs. | 10 (100.0) | 10 (100.0) | 10 (100.0) | 10 (100.0) | 10 (100.0) |
| | 48 hrs. | 10 (100.0) | 10 (100.0) | 10 (100.0) | 10 (100.0) | 10 (100.0) |
| Eco PCO AC | 1 min. | 10 (100.0) | 10 (100.0) | 10 (100.0) | 10 (100.0) | 10 (100.0) |
| (ADL-2-12-B) | 5 min. | 10 (100.0) | 10 (100.0) | 10 (100.0) | 10 (100.0) | 10 (100.0) |
| | 10 min. | 10 (100.0) | 10 (100.0) | 10 (100.0) | 10 (100.0) | 10 (100.0) |
| | 1 hr. | 10 (100.0) | 10 (100.0) | 10 (100.0) | 10 (100.0) | 10 (100.0) |
| | 24 hrs. | 10 (100.0) | 10 (100.0) | 10 (100.0) | 10 (100.0) | 10 (100.0) |
| | 48 hrs. | 10 (100.0) | 10 (100.0) | 10 (100.0) | 10 (100.0) | 10 (100.0) |

TABLE 2-continued

Number of dead termites (% mortality) n = 10 at 1,
5, and 10 minutes and 1, 24, and 48 hours posttreatment.

| Treatment | Posttreatment Time | Replicate 1 | 2 | 3 | 4 | Mean |
|---|---|---|---|---|---|---|
| Untreated | 1 min. | 0 (0.0) | 0 (0.0) | 0 (0.0) | 0 (0.0) | 0 (0.0) |
|  | 5 min. | 0 (0.0) | 0 (0.0) | 0 (0.0) | 0 (0.0) | 0 (0.0) |
|  | 10 min. | 0 (0.0) | 0 (0.0) | 0 (0.0) | 0 (0.0) | 0 (0.0) |
|  | 1 hr. | 0 (0.0) | 0 (0.0) | 0 (0.0) | 0 (0.0) | 0 (0.0) |
|  | 24 hrs. | 9 (90.0) | 9 (90.0) | 9 (90.0) | 9 (90.0) | 9 (90.0) |
|  | 48 hrs. | 10 (100.0) | 10 (100.0) | 10 (100.0) | 10 (100.0) | 10 (100.0) |

EXAMPLE 18

Southern House Mosquito, *Culex pipiens quinquefasciatus*

| | |
|---|---|
| Life Stage: | Adult |
| Experimental Design: | Randomized Complete Block Design |
| Replication: | 4 |
| # Organisms per Replicate: | Variable |

Test Conditions: Mosquito eggs were obtained from the Mosquito Control Research Laboratory, Parlier, Calif. and were reared at Bio Research until the pupal stage. As adult emergence occurred the pupae were transferred into plastic cups. The mosquitoes that emerged in each cup represented one replicate group. Only one group of mosquitoes were treated at a time.

Prior to each spray application the aerosol canisters were tested to insure proper function. The pre-treatment canister weight was recorded. A cup containing a high number of emerged adults was selected and brought into the test chamber (5'×5'×8' walk-in closet), which was maintained at 65 to 75° F., and the door was closed. The lid was removed from the cup allowing the mosquitoes to fly freely within the chamber. After a five-minute acclimation period, any mosquito that appeared unhealthy or unable to fly was removed from the trial. The test materials were then applied. A three second burst was sprayed upwards in all directions. The number of mosquitoes knocked down was recorded at 1, 3, 5, 10, 15, 30 and 60 minutes after treatment. The researcher remained in the closed chamber for the first 15 minutes, then returned for the 30 and 60 minute evaluations. A cloth sheet hung over the doorway prevented the mosquitoes from escaping when the door was opened.

The aerosol canister was weighed again, so the amount of material could be quantified (Table 1). The chamber was then thoroughly cleaned with a 2% bleach solution. A large fan was placed in the open chamber and ran for at least one hour. When the odor of bleach could no longer be detected the chamber was considered ready for the next treatment. The untreated group was tested randomly during the study to assess any effects of unremoved residues.

Evaluation: The number of dead mosquitoes was assessed at 1, 3, 5, 10, 15, 30 and 60 minutes posttreatment. Death was defined as the inability of the organism to move.

Results and Discussion: The test product Eco PCO ACU (ADL-2-12-A) caused 59.2% death within 1 minute after application, but total kill required 60 minutes. The Eco PCO AC (ADL-2-12-B) treatment caused 31.5% death within 1 minute but only caused 84.2% kill by 60 minutes (Table 2).

TABLE 1

Amount of product (grams) dispensed at each spray application - Mosquito.

| Treatment | Replicate 1 | 2 | 3 | 4 | Mean |
|---|---|---|---|---|---|
| Eco PCO ACU (ADL-2-12-A) | 9.5 | 9.8 | 7.9 | 8.9 | 9.0 |
| Eco PCO AC (ADL-2-12-B) | 10.3 | 5.7 | 6.4 | 7.7 | 7.5 |
| Untreated | 0.0 | 0.0 | 0.0 | 0.0 | 0.0 |

TABLE 2

Number of dead mosquitoes per total and % mortality at 1, 3, 5, 10, 15, 30, and 60 minutes posttreatment.

| Treatment | Posttreatment Time | Replicate 1 | 2 | 3 | 4 | Mean |
|---|---|---|---|---|---|---|
| Eco PCO ACU (ADL-2-12-A) | 1 min. | 15/23 | 30/39 | 8/23 | 21/40 | 59.2 |
|  | 3 min. | 19/23 | 30/39 | 11/23 | 24/40 | 67.2 |
|  | 5 min. | 21/23 | 34/39 | 12/23 | 25/40 | 73.6 |
|  | 10 min. | 22/23 | 36/39 | 16/23 | 26/40 | 80.0 |
|  | 15 min. | 23/23 | 36/39 | 18/23 | 29/40 | 84.8 |
|  | 30 min. | 23/23 | 38/39 | 21/23 | 34/40 | 92.8 |
|  | 60 min. | 23/23 | 39/39 | 23/23 | 40/40 | 100.0 |
| Eco PCO AC (ADL-2-12-B) | 1 min. | 12/24 | 7/27 | 5/41 | 22/54 | 31.5 |
|  | 3 min. | 14/24 | 10/27 | 7/41 | 35/54 | 45.2 |
|  | 5 min. | 15/24 | 12/27 | 8/41 | 38/54 | 50.0 |
|  | 10 min. | 19/24 | 16/27 | 9/41 | 41/54 | 58.2 |
|  | 15 min. | 19/24 | 18/27 | 10/41 | 41/54 | 60.3 |
|  | 30 min. | 23/24 | 23/27 | 15/41 | 43/54 | 71.2 |
|  | 60 min. | 23/24 | 24/27 | 28/41 | 48/54 | 84.2 |
| Untreated | 1 min. | 0/29 | 0/47 | 0/42 | 0/56 | 0.0 |
|  | 3 min. | 0/29 | 0/47 | 0/42 | 0/56 | 0.0 |
|  | 5 min. | 0/29 | 0/47 | 0/42 | 0/56 | 0.0 |
|  | 10 min. | 0/29 | 0/47 | 0/42 | 0/56 | 0.0 |
|  | 15 min. | 0/29 | 0/47 | 0/42 | 0/56 | 0.0 |
|  | 30 min. | 1/29 | 1/47 | 0/42 | 0/56 | 0.0 |
|  | 60 min. | 2/29 | 2/47 | 0/42 | 0/56 | 0.0 |

EXAMPLE 19

Pillbug, *Armadillidium vulgare*

| | |
|---|---|
| Life Stage: | Adult |
| Experimental Design: | Randomized Complete Block Design |
| Replication: | 4 |
| # Organisms per Replicate: | 10 |

Holding Conditions: Pillbugs were field collected in Fresno County, Calif. They were held for about 2 hours prior to study initiation. The pillbugs were then transferred into clear plastic cups (7.5 cm high×11 cm dia) and held at 70° F. The cup lids were removed during the test. A circular disc of vinyl flooring was placed in the bottom of each cup, and the pillbugs moved freely over the floor surface. No food or water was provided.

Spray Application: A short burst of the unscented pesticidal composition, or the positive control pesticidal composition was directed at the test organisms. No spray was applied to the untreated control. The spray canister was held 30 cm from the target. Complete spray coverage of the pillbugs and floor surface was observed. The amount of product dispensed was determined by weighing the canister before and after each spray (Table 1).

Evaluation: The number of dead pillbugs was assessed at 1, 5, and 10 minutes and at 1, 24, and 48 hours posttreatment. Death was defined as the inability of the organism to move when probed.

Results and Discussion: One minute after treatment 40% of the pillbugs sprayed with EcoPCO ACU (ADL-2-12-A) were dead, compared to 35% of those sprayed with EcoPCO AC (ADL-2-12-B). Five minutes after treatment all pillbugs sprayed with EcoPCO ACU (ADL-2-12-A) were dead, whereas 82.5% of those sprayed with EcoPCO AC (ADL-2-12-B) were moribund. Ten minutes after treatment all sprayed pillbugs were dead. No mortality occurred in the untreated group during the holding period (Table 2).

TABLE 1

Amount of product (grams) dispensed at each spray application - Pillbug.

| | Replicate | | | | |
|---|---|---|---|---|---|
| Treatment | 1 | 2 | 3 | 4 | Mean |
| Eco PCO ACU (ADL-2-12-A) | 1.3 | 0.9 | 0.7 | 1.2 | 1.0 |
| Eco PCO AC (ADL-2-12-B) | 1.1 | 0.5 | 0.8 | 1.0 | 0.9 |
| Untreated | 0.0 | 0.0 | 0.0 | 0.0 | 0.0 |

TABLE 2

Number of dead pillbugs (% mortality) n = 10 at 1, 5, and 10 minutes and 1, 24, and 48 hours posttreatment.

| Treatment | Posttreatment Time | Replicate 1 | 2 | 3 | 4 | Mean |
|---|---|---|---|---|---|---|
| Eco PCO ACU (ADL-2-12-A) | 1 min. | 1 (10.0) | 4 (40.0) | 5 (50.0) | 6 (60.0) | 4 (40.0) |
| | 5 min. | 10 (100.0) | 10 (100.0) | 10 (100.0) | 10 (100.0) | 10 (100.0) |
| | 10 min. | 10 (100.0) | 10 (100.0) | 10 (100.0) | 10 (100.0) | 10 (100.0) |
| | 1 hr. | 10 (100.0) | 10 (100.0) | 10 (100.0) | 10 (100.0) | 10 (100.0) |
| | 24 hrs. | 10 (100.0) | 10 (100.0) | 10 (100.0) | 10 (100.0) | 10 (100.0) |
| | 48 hrs. | 10 (100.0) | 10 (100.0) | 10 (100.0) | 10 (100.0) | 10 (100.0) |
| Eco PCO AC (ADL-2-12-B) | 1 min. | 3 (30.0) | 4 (40.0) | 3 (30.0) | 4 (40.0) | 4 (35.0) |
| | 5 min. | 9 (90.0) | 8 (80.0) | 7 (70.0) | 9 (90.0) | 8 (82.5) |
| | 10 min. | 10 (100.0) | 10 (100.0) | 10 (100.0) | 10 (100.0) | 10 (100.0) |
| | 1 hr. | 10 (100.0) | 10 (100.0) | 10 (100.0) | 10 (100.0) | 10 (100.0) |
| | 24 hrs. | 10 (100.0) | 10 (100.0) | 10 (100.0) | 10 (100.0) | 10 (100.0) |
| | 48 hrs. | 10 (100.0) | 10 (100.0) | 10 (100.0) | 10 (100.0) | 10 (100.0) |
| Untreated | 1 min. | 0 (0.0) | 0 (0.0) | 0 (0.0) | 0 (0.0) | 0 (0.0) |
| | 5 min. | 0 (0.0) | 0 (0.0) | 0 (0.0) | 0 (0.0) | 0 (0.0) |
| | 10 min. | 0 (0.0) | 0 (0.0) | 0 (0.0) | 0 (0.0) | 0 (0.0) |
| | 1 hr. | 0 (0.0) | 0 (0.0) | 0 (0.0) | 0 (0.0) | 0 (0.0) |
| | 24 hrs. | 0 (0.0) | 0 (0.0) | 0 (0.0) | 0 (0.0) | 0 (0.0) |
| | 48 hrs. | 0 (0.0) | 0 (0.0) | 0 (0.0) | 0 (0.0) | 0 (0.0) |

EXAMPLE 20

Long-Bodied Cellar Spider (*Pholcus phalagiodes*)

| | |
|---|---|
| Life Stage: | Adult |
| Experimental Design: | Randomized |
| Replication: | 10 |
| # Organisms per Replicate: | 1 |

Test Conditions: A site was located in Fresno County, Calif. where cellar spiders were common. The researcher sprayed each spider with the test product and then observed mortality.

Spray Application: A short burst of the unscented pesticidal composition, or the positive control pesticidal composition was directed at the test organisms. No spray was applied to the untreated control. The spray canister was held 30 cm from the target. Complete spray coverage of the spider and webbing was observed. The amount of product dispensed was determined by weighing the canister before and after each spray (Table 1).

Evaluation: The number of dead spiders was assessed at 1, 5, and 10 minutes and at 1 hour posttreatment. Death was defined as the inability of the organism to move when probed.

Results and Discussion: One minute after treatment 70% of the cellar spiders sprayed with Eco PCO ACU (ADL-2-12-A) were dead, compared to none (0%) of those sprayed with Eco PCO AC (ADL-2-12-B). Five minutes after treatment all spiders sprayed with Eco PCO ACU (ADL-2-12-A) were dead, whereas 60% of those sprayed with Eco PCO AC (ADL-2-12-B) were moribund. One hour after the spray application all spiders were dead in the Eco PCO AC treatment. No mortality occurred in the untreated group during the test period (Table 2).

TABLE 1

Amount of product (grams) dispensed at each spray application - Cellar spider.

| Treatment | Replicate | | | | | | | | | | Mean |
| --- | --- | --- | --- | --- | --- | --- | --- | --- | --- | --- | --- |
|  | 1 | 2 | 3 | 4 | 5 | 6 | 7 | 8 | 9 | 10 |  |
| Eco PCO ACU (ADL-2-12-A) | 0.8 | 1.2 | 0.7 | 0.5 | 1.1 | 0.5 | 0.7 | 0.7 | 1.0 | 1.1 | 0.8 |
| Eco PCO AC (ADL-2-12-B) | 0.8 | 0.5 | 1.0 | 0.8 | 0.9 | 1.1 | 0.7 | 0.6 | 0.9 | 0.6 | 0.8 |
| Untreated | 0.0 | 0.0 | 0.0 | 0.0 | 0.0 | 0.0 | 0.0 | 0.0 | 0.0 | 0.0 | 0.0 |

TABLE 2

Number of dead cellar spiders (% mortality) n = 1 at 1, 5, and 10 minutes and 1 hour posttreatment.

| Treatment | Posttreatment Time | Replicate | | | | | | | | | | Mean |
| --- | --- | --- | --- | --- | --- | --- | --- | --- | --- | --- | --- | --- |
|  |  | 1 | 2 | 3 | 4 | 5 | 6 | 7 | 8 | 9 | 10 |  |
| Eco PCO ACU (ADL-2-12-A) | 1 min. | * | * | * | * |  |  | * |  | * | * | 7 (70.0) |
|  | 5 min. | * | * | * | * | * | * | * | * | * | * | 10 (100.0) |
|  | 10 min. | * | * | * | * | * | * | * | * | * | * | 10 (100.0) |
|  | 1 hour | * | * | * | * | * | * | * | * | * | * | 10 (100.0) |
| Eco PCO AC (ADL-2-12-B) | 1 min. |  |  |  |  |  |  |  |  |  |  | 0 (0.0) |
|  | 5 min. |  |  | * | * | * | * |  | * |  | * | 6 (60.0) |
|  | 10 min. | * | * | * | * | * |  | * | * |  | * | 8 (80.0) |
|  | 1 hour | * | * | * | * | * | * | * | * | * | * | 10 (100.0) |
| Untreated | 1 min. |  |  |  |  |  |  |  |  |  |  | 0 (0.0) |
|  | 5 min. |  |  |  |  |  |  |  |  |  |  | 0 (0.0) |
|  | 10 min. |  |  |  |  |  |  |  |  |  |  | 0 (0.0) |
|  | 1 hour |  |  |  |  |  |  |  |  |  |  | 0 (0.0) |

* spider dead

EXAMPLE 21

Wolf Spider (family: *Lycosidae*), *Lycosa* sp.

| Life Stage: | Adult |
| --- | --- |
| Experimental Design: | Randomized |
| Replication: | 10 |
| # Organisms per Replicate: | 1 |

Test Conditions: Wolf spiders were field collected from the lawn at the Bio Research facility. They were held for 2 hours prior to study initiation. The spiders were then transferred into clear plastic cups (7.5 cm high×11 cm dia) and held at 70° F. One spider was placed into each cup. The sides of the cups were treated with Fluon and a circular disc of vinyl flooring was placed in the bottom of each cup. The spiders moved freely over the floor surface. No food or water was provided. The researcher sprayed each spider with the test product and then observed mortality.

Spray Application: A short burst of the unscented pesticidal composition, or the positive control pesticidal composition was directed at the test organisms. No spray was applied to the untreated control. The spray canister was held 30 cm from the target. Complete spray coverage of the spider and flooring was observed. The amount of product dispensed was determined by weighing the canister before and after each spray (Table 1).

Evaluation: The number of dead spiders was assessed at 1, 5, and 10 minutes and at 1 and 24 hours posttreatment. Death was defined as the inability of the organism to move when probed.

Results and Discussion: One minute after treatment 50% of the wolf spiders sprayed with Eco PCO ACU (ADL-2-12-A) were dead, compared to 90% of those sprayed with Eco PCO AC (ADL-2-12-B). Five minutes after treatment all spiders sprayed with Eco PCO ACU or Eco PCO AC were dead. No mortality occurred in the untreated group during the test period (Table 2).

TABLE 1

Amount of product (grams) dispensed at each spray application - Wolf spider.

| Treatment | Replicate | | | | | | | | | | Mean |
| --- | --- | --- | --- | --- | --- | --- | --- | --- | --- | --- | --- |
|  | 1 | 2 | 3 | 4 | 5 | 6 | 7 | 8 | 9 | 10 |  |
| Eco PCO ACU (ADL-2-12-A) | 0.9 | 0.7 | 0.4 | 0.8 | 1.0 | 0.9 | 0.9 | 1.4 | 0.9 | 0.9 | 0.9 |
| Eco PCO AC (ADL-2-12-B) | 1.1 | 1.2 | 1.1 | 0.6 | 1.0 | 0.6 | 1.0 | 0.5 | 0.7 | 0.6 | 0.8 |
| Untreated | 0.0 | 0.0 | 0.0 | 0.0 | 0.0 | 0.0 | 0.0 | 0.0 | 0.0 | 0.0 | 0.0 |

TABLE 2

Number of dead wolf spiders (% mortality) n = 1 at 1, 5, and 10 minutes and 1 and 24 hours posttreatment.

| Treatment | Posttreatment Time | 1 | 2 | 3 | 4 | 5 | 6 | 7 | 8 | 9 | 10 | Mean |
|---|---|---|---|---|---|---|---|---|---|---|---|---|
| Eco PCO ACU | 1 min. | * | * |   |   | * |   |   | * |   | * | 5 (50.0) |
| (ADL-2-12-A) | 5 min. | * | * | * | * | * | * | * | * | * | * | 10 (100.0) |
|  | 10 min. | * | * | * | * | * | * | * | * | * | * | 10 (100.0) |
|  | 1 hour | * | * | * | * | * | * | * | * | * | * | 10 (100.0) |
|  | 24 hour | * | * | * | * | * | * | * | * | * | * | 10 (100.0) |
| Eco PCO AC | 1 min. | * | * | * | * | * | * | * | * |   | * | 9 (90.0) |
| (ADL-2-12-B) | 5 min. | * | * | * | * | * | * | * | * | * | * | 10 (100.0) |
|  | 10 min. | * | * | * | * | * | * | * | * | * | * | 10 (100.0) |
|  | 1 hour | * | * | * | * | * | * | * | * | * | * | 10 (100.0) |
|  | 24 hour | * | * | * | * | * | * | * | * | * | * | 10 (100.0) |
| Untreated | 1 min. |   |   |   |   |   |   |   |   |   |   | 0 (0.0) |
|  | 5 min. |   |   |   |   |   |   |   |   |   |   | 0 (0.0) |
|  | 10 min. |   |   |   |   |   |   |   |   |   |   | 0 (0.0) |
|  | 1 hour |   |   |   |   |   |   |   |   |   |   | 0 (0.0) |
|  | 24 hour |   |   |   |   |   |   |   |   |   |   | 0 (0.0) |

* spider dead

As can be seen from the above discussion, the pesticidal combinations of active compounds according to the present invention are markedly superior to known pesticidal agents/active compounds conventionally used for control of pests. Although illustrative embodiments of the invention have been described in detail, it is to be understood that the present invention is not limited to those precise embodiments, and that various changes and modifications can be effected therein by one skilled in the art without departing from the scope and spirit of the invention as defined by the appended claims.

What is claimed is:

1. A method for killing or controlling invertebrates comprising:
applying a pesticidally-effective amount of a pesticidal composition to invertebrates or to a locus where killing or control of invertebrates is desired, wherein (i) the invertebrates are selected from the group consisting of ants, cockroaches, spiders, fleas, ticks, earwigs, pillbugs, beetles, flies, crickets, mosquitoes, and wasps, and (ii) the pesticidal composition is unscented and comprises an inert carrier and a pesticidally active ingredient consisting of benzyl alcohol and phenethyl propionate.

2. The method of claim 1, wherein the invertebrates are ants.

3. The method of claim 1, wherein the invertebrates are fleas.

4. The method of claim 1, wherein the invertebrates are earwigs.

5. The method of claim 1, wherein the invertebrates are ticks.

6. The method of claim 1, wherein the invertebrates are beetles.

7. The method of claim 1, wherein the invertebrates are flies.

8. The method of claim 1, wherein the invertebrates are crickets.

9. The method of claim 1, wherein the invertebrates are cockroaches.

10. The method of claim 1, wherein the invertebrates are wasps.

11. The method of claim 1, wherein the invertebrates are mosquitoes.

12. The method of claim 1, wherein the invertebrates are pillbugs.

13. The method of claim 1, wherein the invertebrates are spiders.

14. The method of claim 1, wherein the active ingredient is present in the pesticidal composition in an amount of from about 0.01% to about 10% by weight.

15. The method of claim 14, wherein the active ingredient is present in the pesticidal composition in an amount of from about 0.01% to about 1.0% by weight.

16. The method of claim 1, wherein the carrier is a member selected from the group consisting of: a wettable powder, a dry powder, a dust, an aerosol propellant, and water having at least one emulsifier therein.

* * * * *